US006280431B1

(12) United States Patent
Domkowski et al.

(10) Patent No.: US 6,280,431 B1
(45) **Date of Patent: *Aug. 28, 2001**

(54) STERILE FORMED, FILLED AND SEALED FLEXIBLE CONTAINER AND DRAINING ADMINISTRATION PORT THEREFOR

(75) Inventors: John Domkowski, Kenosha, WI (US); Ron Coules, Punk Gorda, FL (US); Peter Carveth, Mountain Home, AK (US); Walter T. Szempruch, Gurnee; Kent D. Abrahamson, Libertyville, both of IL (US)

(73) Assignee: Abbott Laboratories, Abbott Park, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/178,323

(22) Filed: Oct. 23, 1998

(51) Int. Cl.[7] .................... A61B 19/00; A61M 5/32
(52) U.S. Cl. .................... 604/411; 604/408; 604/905
(58) Field of Search .................... 604/403–416, 604/533, 539, 905; 383/200, 202, 59, 63, 64, 66, 67, 78, 93, 94

(56) References Cited

U.S. PATENT DOCUMENTS 3,788,374 * 1/1974 Saijo .................... 150/1
5,514,123 5/1996 Adolf et al. .
5,755,712 * 5/1998 Szempruch et al. .................... 604/403

FOREIGN PATENT DOCUMENTS 9314736 8/1993 (WO) .
9422385 10/1994 (WO) .

* cited by examiner

*Primary Examiner*—Richard K. Seidel
*Assistant Examiner*—Jennifer Maynard
(74) *Attorney, Agent, or Firm*—Beth A. Vrioni

(57) ABSTRACT

A formed, filled, and sealed flexible container is provided with an attached port assembly. The container is formed from film folded to define opposing sidewalls which are sealed to define a chamber for sterile fluid. A hollow, tubular port member is provided with a V-shaped saddle and is sealed to the bottom of the container. The film at the bottom of the container is received in the saddle. A unique shoulder is defined by the tubular port member. The film is sealed to the shoulder and to the saddle of the port member. A hollow penetrator element is slidably disposed within the port member and is movable between a retracted position and an advanced position to puncture the film whereby fluid can flow out of the container. Internal formations are provided to guide and to limit the movement of the penetrator element. The container film may be provided with a crease along the bottom of the container.

9 Claims, 12 Drawing Sheets

STERILE FORMED, FILLED AND SEALED FLEXIBLE CONTAINER AND DRAINING ADMINISTRATION PORT THEREFOR

FIELD OF THE INVENTION

The present invention relates to a sterile formed, filled and sealed flexible solution container with an attached administration port system which is effectively sealed to the container and which accommodates complete draining of the solution.

BACKGROUND OF THE INVENTION

Various foodstuffs, liquids, and other degradable material can be sterilely packaged in pouch-type flexible containers made from webs of flexible film that are folded and sealed together along the peripheral side edges. This type of flexible packaging is commonly referred to as a form, fill, and seal package. There are a number of advantages to these pouch-type flexible containers, including low weight, durability, and low cost fabrication. Some medical solutions have also been sterilely packaged in pouch-type flexible containers of the form, fill, and seal type.

One disadvantage of these pouch-type flexible containers for medical solution use is that it is difficult to make a sterile connection to the flexible container for withdrawing the contents in a sterile manner. The wall material of the container is flexible and lacks rigidity. Thus it is difficult to obtain a liquid-tight and leakproof connection through the flexible wall using traditional medical connectors such as needles or piercing pins.

Traditionally, it has been necessary for flexible solution containers used for parenteral solutions to include administration ports to facilitate sterile and liquid-tight access to the solution. These pre-formed, administration ports are often molded from a suitable medical grade thermoplastic material. The usual considerations for the material employed in the administration ports are the ease of molding and the capability to be securely bonded to the flexible film walls of the container. For example, a "boat" administration port may be sealed (by known thermal bonding processes) between the two opposed sides or walls of the flexible film container so as to form a flexible solution container with an administration port. Ultrasonic welding or solvent bonding may also be used to seal the boat port to the container.

The majority of flexible films used for flexible solution containers are monolayer PVC films. Recently, some multiple-layer, extrusion-laminated or adhesive-laminated films have been used in form, fill, and seal packaging for fabricating flexible solution containers. The inner, solution-contacting film layer must be substantially inert to the solution. Also, the inner layer of the film must be readily bondable to itself when it folded over. Furthermore, the outer layer of the film must be bondably compatible with the plastic material used for the attachable administration port. The outer layer of the laminated film must be durable and also compatible with other materials that may contact, or be attached to, the outside surface. If neither the inner nor outer layer has the desired solution-maintaining characteristics and barrier characteristics, such as a low moisture and/or low oxygen permeability, then additional film layers may be required between the inner and outer layers.

A primary disadvantage of known flexible solution containers which include the above-described inserted port construction is that the port material typically has a higher oxygen permeability than the film material; that is, the port structure can be characterized as acting like a "hole" in the sealed bag material. The permeability characteristic of the port material is much greater than the permeability characteristic of the laminated film used to make the flexible container. Thus, the administration port of known flexible solution containers is often the weakest part of the barrier function of the container. This factor becomes extremely important for certain medical solutions which are sensitive (i.e., deleteriously affected by) oxygen or other penetrating gases, for example.

In the past, attempts to overcome the above-discussed deficiencies have been made by overwrapping the flexible solution container, and/or the administration ports, with a low permeability overwrap material. While this redundancy in packaging may provide the desired barrier characteristics, the overwrap material introduces two important disadvantages. First, there is the additional cost to fabricate, and later dispose of, the overwrap. Second, there is concern that extractables from the overwrap material may migrate into the contained solution during post-filling procedures, such as during a heat sterilization process or even during shelf life.

Pre-formed administration ports constitute potential places of leakage and are potential points of contaminant ingress in an otherwise sealed, durable, flexible container. Moreover, the ports make it more difficult to arrange an outer protective overwrap package around the flexible container. Also, the protective overwrap only initially prevents the packaged solution from losing its potency due to evaporation or diffusion. When the overwrap is removed or breached, the installed administration ports in the film essentially function as an undesirable breaches or "holes" in the barrier characteristics of the flexible container for certain sensitive drugs.

For example, due to the sensitivity of certain solutions to oxygen, such as amino acids, it is desirable to fabricate the flexible solution containers for the parenteral administration of these solutions from materials that minimize the permeation of oxygen. The gas permeation properties of the flexible container film can be easily controlled by the choice of film material(s) per se.

On the other hand, the oxygen permeation properties of materials conventionally used for the port structure per se typically do not have low oxygen permeation properties, and the gas permeation properties of such materials are not as easily controlled. Thus, it would be desirable to use the film, with its good gas barrier properties, to provide both the solution contacting surface and a pierceable diaphragm in the administration port system so that the poorer barrier properties of a conventional system material do not contribute to gas migration into or out of the flexible container. However, various known flexible containers having preformed, rigid port systems sealed between the film layers of the flexible container cannot function in such a manner.

Moreover, some known flexible container and administration port systems often include an entry port in addition to the administration port. The entry ports are likewise inserted between film layers at the container perimeter seal. Each port thus constitutes a breach or "hole" through an otherwise effective perimeter barrier.

A pierceable diaphragm can be provided in some administration ports to prevent an outflow of solution. During packaging, the flexible container may be filled through the entry port. After filling, the entry port is sealed, but the port, and specifically the exposed port material, is the potential weak point for compromising the barrier characteristics.

Flange ports are an alternative to inserted ports and may be advantageously sealed to a film surface. However, in many of flexible solution containers produced by known form, fill, and seal processes, the use of flange ports does not remove the barrier deficiency. Consider, for example, the flexible parenteral solution container that includes a flange-sealed port assembly as disclosed in U.S. Pat. No. 4,695,337 to Christine and in U.S. Pat. No. 4,779,397 to Christine et al. A major disadvantage of the disclosed flexible solution container is that the flexible film barrier of the flexible container is purposefully breached during the assembly steps to mount and seal the administration port or fitment to the inside surface of the flexible container, as seen, for example, in FIGS. 4*a*–4*b* of the patents.

Thus, due to the inherent breaches or "holes" in the film barriers of various known form, filled, and sealed flexible solution containers in current use, parenteral solutions may be subjected to degradation during the shelf life of the product solution. While an overwrap may provide some protection for the flexible container and for the port administration system from contamination or degradation during shelf life, the overwrap introduces additional concerns that manufacturers are increasingly seeking to avoid.

Thus, it would be desirable to utilize an unbreached and completely intact film in a form, filled, and sealed flexible solution container as the primary barrier for a medical solution packaged in a flexible solution container, and especially for certain oxygen-sensitive or other gas-sensitive parenteral solutions.

It would also be advantageous to provide a form, filled, and sealed flexible container having integral barrier characteristics without any compromises in the barrier characteristics of the film material used for the flexible solution container.

The Abbott Laboratories U.S. Pat. No. 5,334,180 discloses a sterile formed, filled, and sealed flexible solution container in which the container film defines a pierceable diaphragm that is sealed across the inlet end of an attached tubular port member 50. The film defines a U-shaped trough having a bottom surface 40 which includes a stretched fluid sump 30 and which is heat-sealed to a correspondingly shaped saddle flange 56 of the port member 50. A penetrator element or piercing element 60 is slidably disposed within the tubular port member and is adapted to be pushed inwardly by a conventional piercing pin so that the penetrator element reliably pierces the portion of the container wall film to which the tubular port member is sealed.

While this arrangement functions satisfactorily with various film materials and film wall designs, it would be desirable to provide an even more improved arrangement which could accommodate container films that have a very high resistance to penetration (owing, for example, to the composition of the film and/or to the thickness of the film). In particular, it would be beneficial if an improved design could be provided for establishing a very strong attachment seal of such penetration-resistant film to the tubular port member so as to reduce the likelihood that the film would merely stretch rather than be punctured and/or that the seal between the film and port member would fail as the penetrator element pushes against the diaphragm part of the film.

In addition, it would be desirable to provide an improved arrangement that could accommodate a wide variety of conventional piercing pins having different lengths so that the advancement of the penetrator element by the piercing pin would result in a minimum projection of the penetrator element into the container interior and thereby reduce the likelihood that the interior end of the penetrator element would damage, or otherwise contact, the adjacent sidewalls of the container.

It would also be beneficial to provide a form, filled, and sealed flexible container that includes an attached administration port system that is accessible by a variety of administration piercing pins, including center point pins, beveled pins, and blunt pins, and it would be beneficial to provide such a port system that is compatible with the various lengths and other dimensions of the most common of these administration pins.

It would also be desirable to provide a flexible container that allows the maximum amount of solution to be readily, completely, and easily delivered in a sterile manner from the container. To this end, an improved administration port system should be free of, or at least minimize, pockets or dam features that would prevent complete draining of the container through the port.

Finally, it would be desirable to provide an improved port administration system that can be readily attached to a flexible container with a high integrity seal and reduced distortion while also accommodating the location of the port along the fold of the container film.

SUMMARY OF THE INVENTION

The present invention relates to a sterilely formed, sterilely filled, and sterilely sealed, flexible package for fluid. The package includes a container formed from a sheet of flexible film folded over so that a first portion of the inner surface of the sheet faces a second portion of the inner surface of the sheet. This defines two, opposed sidewalls of the container. The facing portions of the sidewalls of the sheet are sealed together to define a sealed inner chamber adjacent the fold.

According to one aspect of the present invention, a port assembly is provided for use with the flexible container. The port assembly includes a hollow tubular port member having a distal discharge end and a proximal inlet end. The port member defines an annular seal shoulder adjacent the inlet end. The seal shoulder is recessed in one embodiment. In another embodiment, the seal shoulder includes a planar annulus and an adjacent, annular groove or other arcuate surface. The exterior surface of the container film is heat-sealed against the seal shoulder to define inwardly thereof a generally circular, pierceable diaphragm.

A hollow penetrating element is slidably disposed in the tubular port member for movement between a retracted position away from the inlet end and an advanced position adjacent the inlet end to shear or puncture the film diaphragm whereby fluid can flow out of the inner chamber through the hollow penetrating element and port member.

According to another aspect of the invention, a port assembly is provided for a flexible container which is formed from the film that is folded to define a trough from which extend two opposing sidewalls having portions which are sealed together to define an inner chamber adjacent the trough. The port assembly includes a hollow, tubular port member having a discharge end and an inlet end. The port member has a generally V-shaped saddle around the inlet end for sealing the port member to the exterior surface of the film at the bottom of the trough. A hollow penetrator element is slidably disposed in the tubular port member for movement between a retracted position away from the inlet end and an advanced position adjacent the inlet end to shear or puncture the film at the bottom of the trough whereby fluid can flow out of the inner chamber through the hollow penetrator element and port member.

According to still another aspect of the invention, a port assembly is provided for use with a flexible container formed from film folded to define opposing sidewalls having portions which are sealed together to define an inner chamber. The port assembly has a hollow tubular port member with a distal discharge end and a proximal, inlet end which can be heat-sealed to the exterior surface of the film. A hollow penetrator element is slidably disposed in the tubular port member for movement between a fully retracted position away from the inlet end and a fully advanced position adjacent the inlet end to puncture the film whereby fluid can flow out of the inner chamber through the hollow penetrator, element and port member. According to this further aspect of the invention, the tubular port member has (1) an internal, proximal formation having an abutment shoulder defining a frustoconical surface against which a portion of the penetrator element abuts when the penetrator element is at the advanced position, (2) an internal, distal formation having an abutment shoulder defining a frustoconical surface which is engaged by a portion of the penetrator element when the penetrator element is in the fully retracted position, and (3) an intermediate formation between the proximal and distal formations for guiding the penetrator element through an initial part of the travel of the penetrator element as the penetrator element moves away from the fully retracted position toward the fully advanced position.

One or more of the above-described aspects of the present invention, when incorporated in a tubular port member and/or flexible package containing a tubular port member, can offer a number of advantages. These include a stronger attachment or seal between the container film and port member, a package that can exhibit better gas barrier properties, a package with a bottom configuration that accommodates substantially complete draining of the fluid through the port member, a package which accommodates a variety of conventional piercing pins, and a package which minimizes the likelihood of damaging the inside of the container when it is punctured.

DESCRIPTION OF THE PREFERRED EMBODIMENTS

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

For ease of description, the components of this invention are described in a normal (upright) operating position, and terms such as upper, lower, horizontal, etc., are used with reference to this position. It will be understood, however, that the components of this invention may be manufactured, stored, transported, and sold in an orientation other than the position described.

Figures illustrating some of the components of the invention and of a manufacturing system therefor show some features or elements that are known and that will be recognized by one skilled in the art. The detailed descriptions of such elements are not necessary to an understanding of the invention, and accordingly, are herein presented only to the degree necessary to facilitate an understanding of the novel features of the present invention.

The components of this invention are intended to be used with certain other conventional components, the details of which, although not fully illustrated or described, will be apparent to those having skill in the art and an understanding of the necessary functions of such other conventional components.

Figure 1:
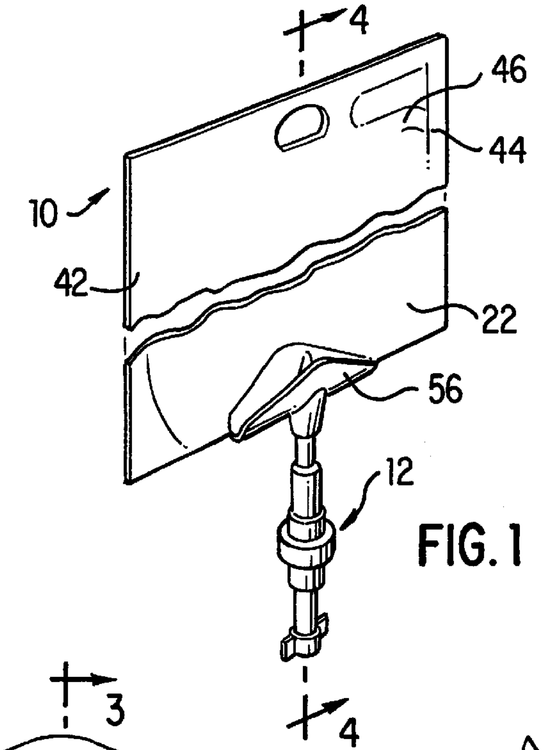
FIG. 1 is a perspective view of a package incorporating the features of a first embodiment of the present invention.
Figure 5:
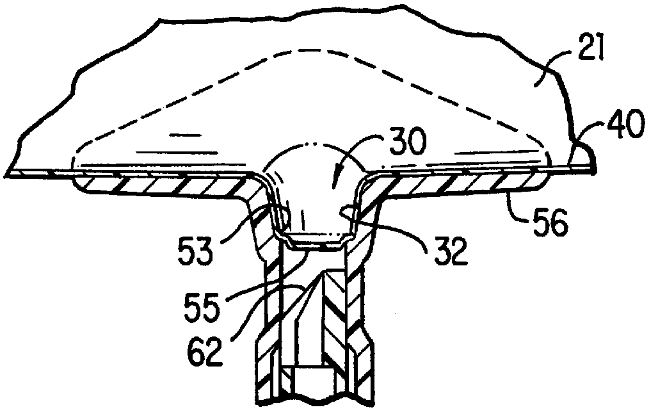
FIG. 5 is a cross-sectional view taken generally along the plane 5—5 in FIG. 4.

FIGS. 1 and 5 show a flexible solution container 10 and port assembly 12 for maintenance and delivery of a sterile medical solution or fluid. The flexible container 10 is fabricated from a sheet of flexible film. The film may be a multi-layer film, such as, for example, an extrusion-laminated film or an adhesive-laminated film. Such a laminated film may have a first bondable surface layer (e.g., a gas barrier layer), a thermal stability layer, appropriate bonding layers, and an outer bondable surface layer.

Figure 4:
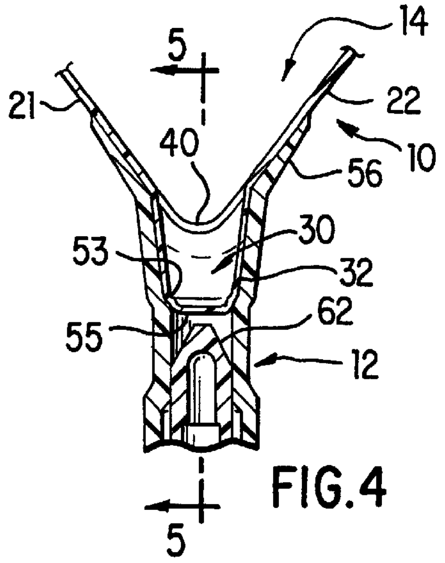
FIG. 4 is a greatly enlarged, fragmentary, cross-sectional view taken generally along the plane 4—4 in FIG. 1.

The film is folded, sealed along the sides, filled, and then sealed along the top to form a sealed, fluid-filled, inner chamber 14 (FIG. 4).

The components of the port assembly 12 are molded of suitable plastic materials, and the assembly 12 is attachable by a saddle or flange 56 to the outer surface of the container 10, preferably by a thermal bonding process.

Figure 12:
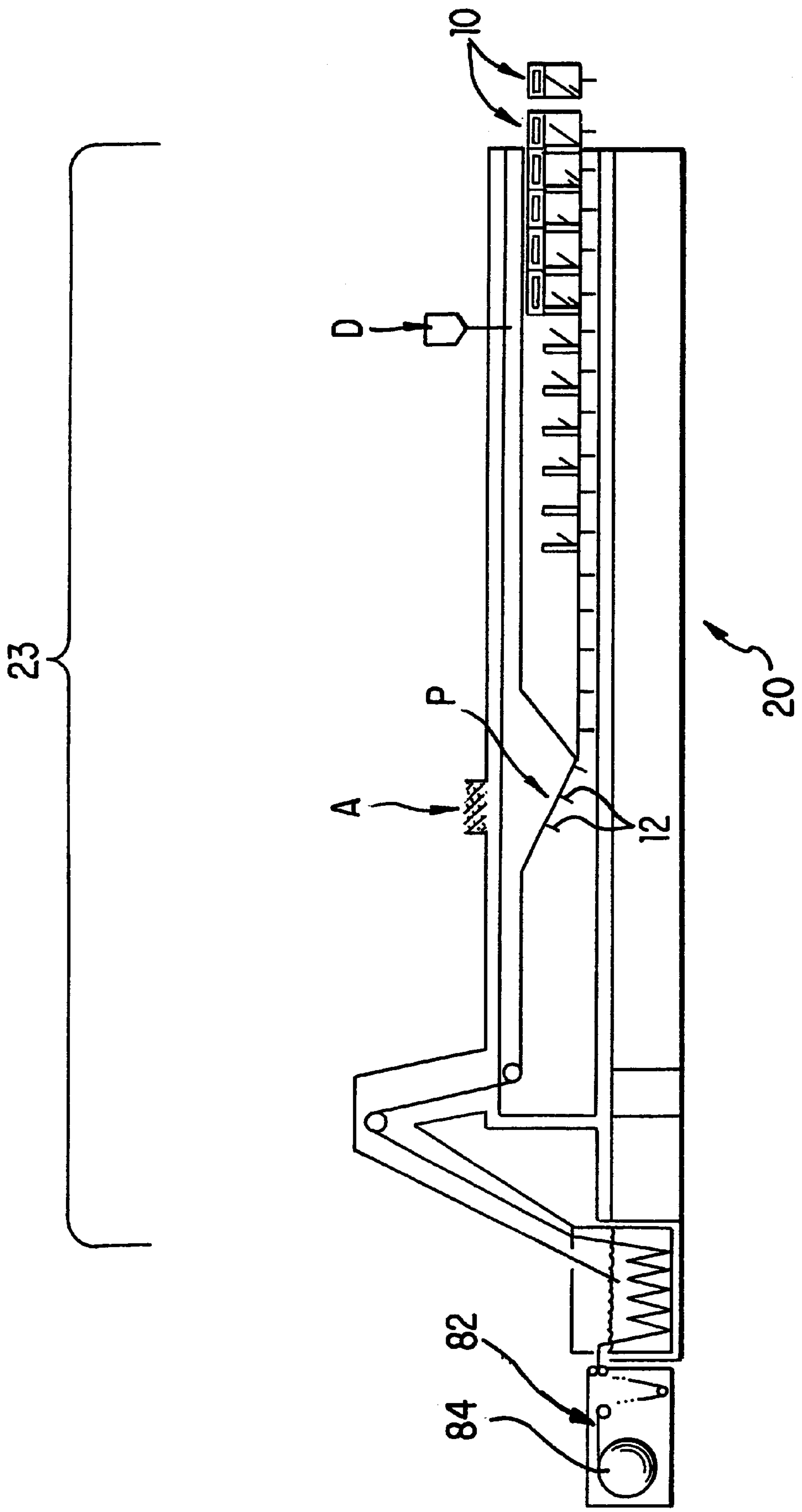
FIG. 12 is a schematic diagram illustrating the operation of a form, fill, and seal packaging machine that can be used to fabricate the package of the present invention.

The flexible container 10 is preferably manufactured in a form, fill, and seal packaging machine 20 as schematically depicted in FIG. 12. The forming of the flexible container 10, the filling of it with a sterile solution, and the sealing of the flexible container is performed in a sterile core environment 23 associated with the packaging machine. The product solution is pre-sterilized outside of the sterile core environment 23. The product solution is maintained sterile as it is filled and sealed in the flexible container.

The port assembly 12 is also pre-sterilized outside of the sterile core environment 23 and is attached to the flexible container 10 in the sterile core environment. The completed package thus comprises a sterile solution in a sterile container 10 with an attached sterile port assembly 12 that is suitable for medical use, such as for parenteral fluid administration.

The film from which the container 10 is made may be in the form of a sheet 82 which is initially horizontally flat and which enters the form, fill, and seal packaging machine. An imaginary or theoretical, longitudinal and vertically oriented, middle plane intersects the film sheet 82 to define a "saddle" line and longitudinally divides the film sheet 82 into substantially equal and mirror-image first and second sidewall portions 21 and 22, respectively.

The port assemblies 12 are attached at locations along the saddle line to the adjacent regions of the sidewall portions 21 and 22. Each port assembly 12 is attached to the sidewall portions 21 and 22 of the adjacent sheet 82 by deforming the sheet 82 along the saddle line into the upper, open end of the port assembly 12 to define a sump 30 (FIG. 5) within the upper, open end of the port assembly 12. Each sump 30 is formed as the sheet 82 is attached to a port assembly 12 such that the longitudinal axis of each sump 30 is perpendicular to, and intersects, the saddle line. Preferably, a thermoforming process is employed to attach each port assembly 12 to the sheet 82 which results in the formation of the sump 30 nested within the upper, open end of the port assembly 12. As a port assembly 12 is attached to the sheet 82, a discrete, relevant portion of the sheet 82 is heated and permanently stretched outwardly into the port assembly 12 to form the sump 30 with a transverse closure wall or diaphragm 55 that is adapted to be penetrated or sheared by a penetrator element as described in detail later.

The sump 30 preferably has a smooth interior surface above the diaphragm 55. As described in detail hereinafter, the sump 30 is formed during attachment of the port assembly 12 to the film 82 by permanently stretching the film 82 beyond its recovery limit with a heated forming die. The saddle flange 56 of port assembly 10 is attached by thermobonding or fusing to the outside bondable surface of the film 82 at the sump 30.

During the container fabrication process, the first and second sidewall portions of the film sheet 82 are inwardly folded over the saddle line so as to form a trough 40 (FIGS. 4 and 5). In a preferred form, the sidewall portions of the sheet 82 are folded over after the port assemblies are attached (i.e., downstream of the forming die which attaches the port assemblies 12 to the sheet 82). With reference to FIG. 1, the opposed first and second film sidewall portions 21 and 22, respectively, are sealed together along a first sealing line extending from, and generally perpendicular to, the bottom trough 40 so as to form a first transverse side seal 42. The sidewall portions are sealed together along a second sealing line generally parallel to the first line, but an equal distance on the other side of the fluid sump 30, so as to form a second transverse side seal 44. The first side seal 42, the bottom trough 40, and the second side seal 44 together form an open pouch.

The open pouch is formed within the sterile core environment 22 and is contacted only by the sterile filtered air of the sterile core environment. The pouch may be optionally flushed with a special flushing agent if it is to be filled with a drug that is sensitive to a component of air. Subsequently, the pouch is filled with the sterile solution, and the top portion of the pouch is sealed together along a third sealing line 46 so as to form the hermetically sealed, fluid-filled, inner chamber 14 between the first and second film portions 21 and 22, respectively.

Figure 2:
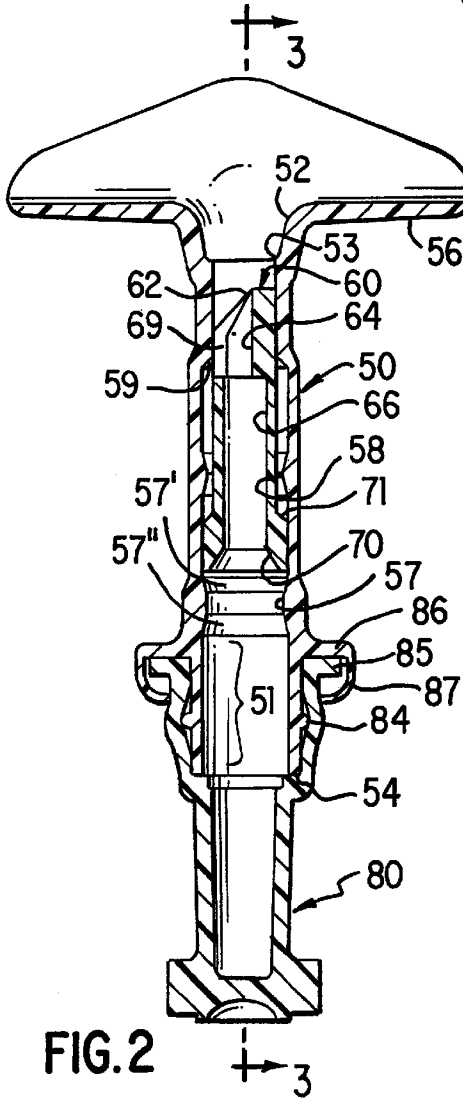
FIG. 2 is a greatly enlarged, cross-sectional, elevational view of a first embodiment of the tubular port member of the present invention.
Figure 3:
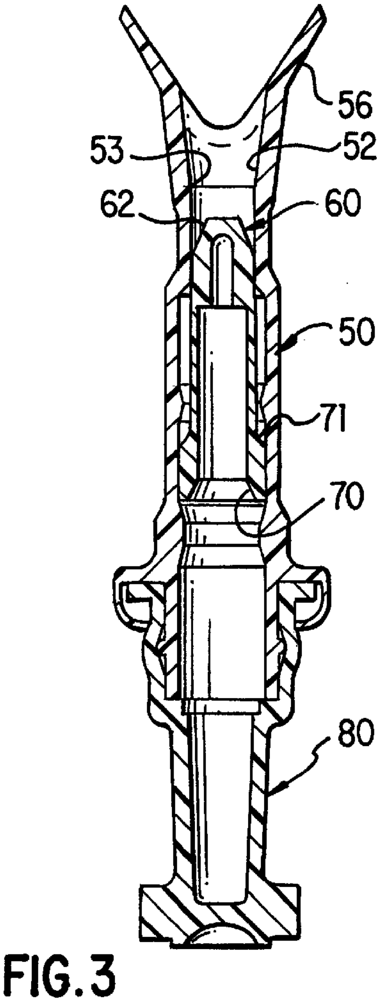
FIG. 3 is a view taken generally along the plane 3—3 in FIG. 2.

Referring now to FIGS. 2–3, the port assembly 12 includes a tubular member 50 projecting from the saddle 56, a cylindrical penetrator element 60, and a cap or cover member 80. The tubular port member 50 has a proximal, inlet end 52 merging with the saddle 56 and has a distal, discharge end 54 which is occluded by the cap 80 until just prior to use. The member 50 is preferably molded from a heat-bondable, medical grade thermoplastic. Preferably, the material of the port member 50 is either the same as, or is at least compatible with, and bondable to, the outer surface of the film 82. In one contemplated embodiment, the tubular port member 50 is preferably injection molded from an olefin.

The tubular port member 50 may be characterized as including the integral saddle or flange 56 that surrounds the open, proximal, inlet end 52. The saddle or flange 56 is preferably V-shaped in cross section (FIG. 3). The saddle 56, at the open end 52, has a contoured internal shape which is the same as the outwardly stretched fluid sump 30 of the flexible container.

Figure 6:
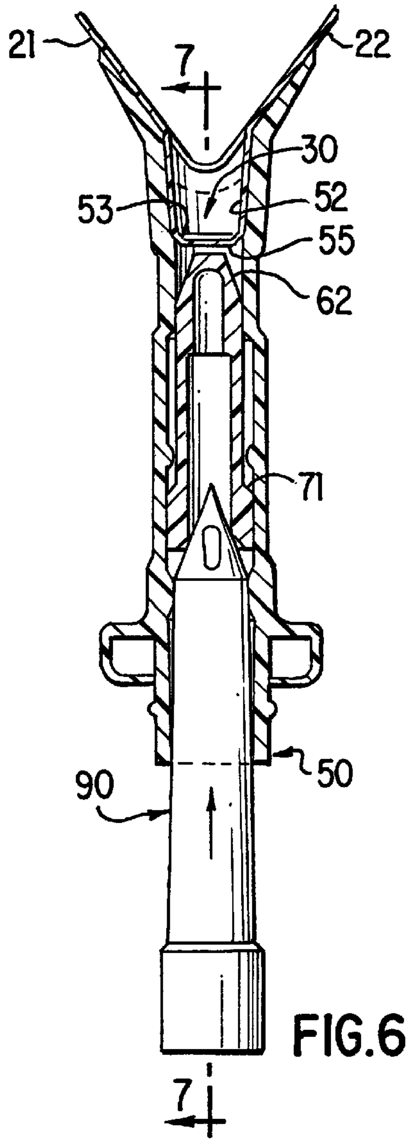
FIG. 6 is a fragmentary, cross-sectional view similar to FIG. 5, but FIG. 6 shows the cover removed from the lower, discharge end of the tubular port member and a conventional piercing pin partially inserted.
Figure 9:
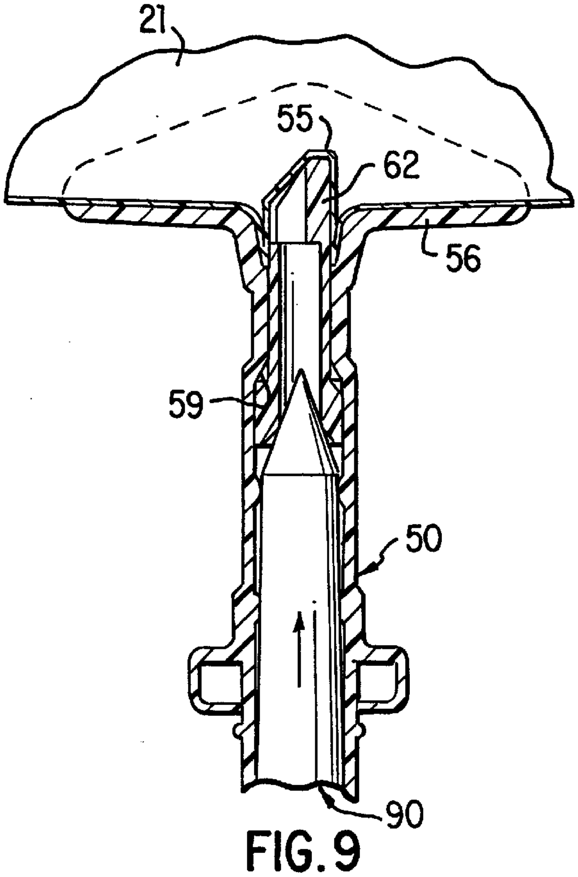
FIG. 9 is a fragmentary, cross-sectional view taken generally along the plane 9—9 in FIG. 8.
Figure 8:
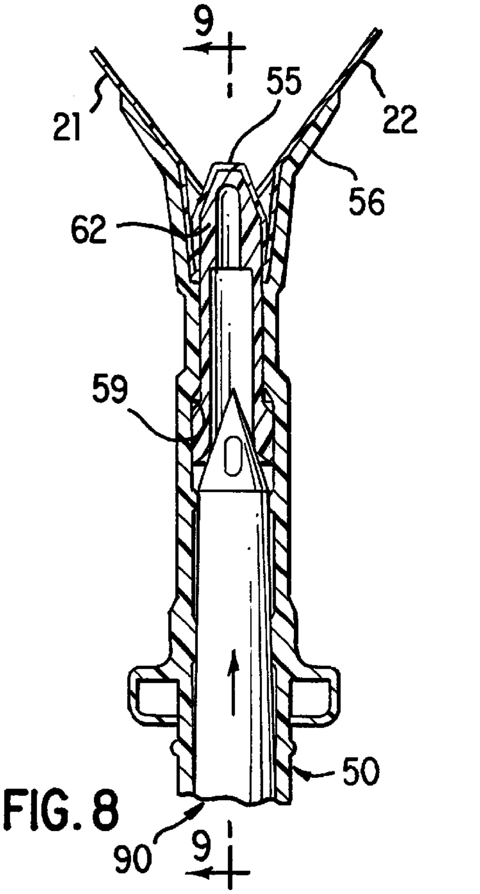
FIG. 8 is a view similar to FIG. 6, but FIG. 8 shows the conventional piercing pin further inserted into the tubular port member to move a penetrator element toward a fully advanced position.

As shown in FIG. 6, the contoured saddle 56 is sealed to the film sides 21 and 22 around the open, inlet end 52 of the tubular portion member 50 so that there is an annular (i.e., circumferential) fluid seal around the diaphragm 55 between the inner surface of the flange 56 and the outer surface of the film at the fluid sump 30. Preferably, the tubular member 50 defines a step or shoulder 53 (FIG. 5) against which the periphery of the diaphragm 55 bears and is sealed. In the presently contemplated first embodiment of the tubular port member 50, the shoulder 53 has a width of about 0.01 inch.

The seal shoulder 53 is preferably a circular annulus. The interior surface of the port member 50 above the shoulder 53 defines a suitable shape. For example, although not presently preferred, the surface may become slightly ellipsoidal with increasing distance upwardly away from the circular seal shoulder 53. Preferably, however, the surface of the first embodiment of the port member 50 above the shoulder 53 is frustoconical for simplicity and reliability in manufacturing.

Figure 7:
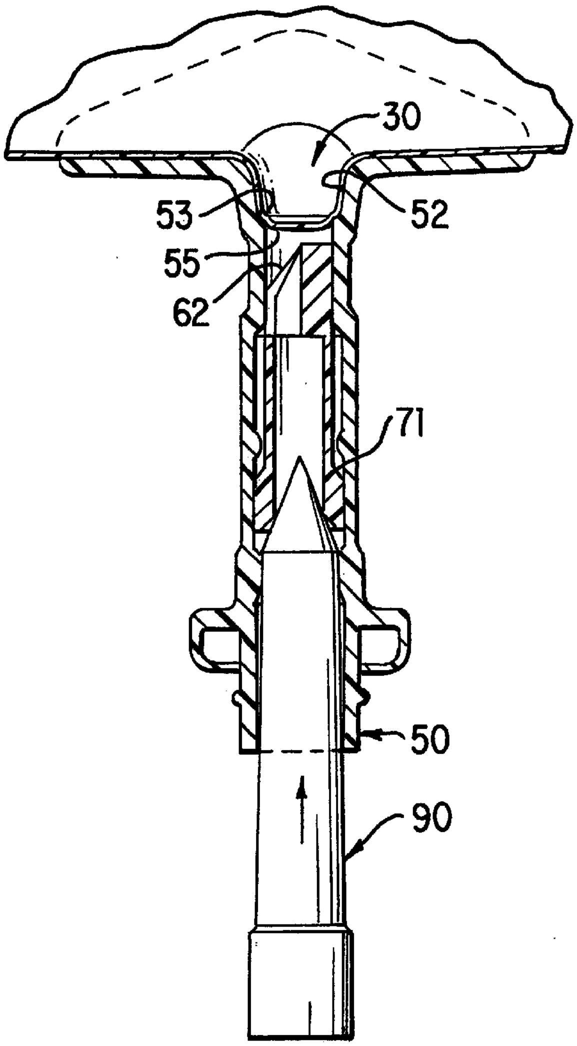
FIG. 7 is a fragmentary, cross-sectional view taken generally along the plane 7—7 in FIG. 6.

The distal discharge end 54 of the tubular port member 50 includes an administration fitment or access fitment 51 (FIG. 2) that is fluid tight when connected with most conventional medical fluid connectors, such as piercing pins (shown in FIGS. 6 and 7). The removable cover or cap 80 is provided for closing the end 54 and maintaining the sterility of the fitment 51 at the end 54. The cover 80 is preferably made from an injection molded material or from a compression set, resilient, elastomeric material. As shown in FIG. 2, the cover 80 has a wall which frictionally engages an annular bead 84 on the port member 50.

The inner end of the cover or cap 80 has a radial flange 85. The tubular port member 50 is initially molded with a radial flange 86 and a thinner, radially extending skirt 87 which, after installation of the cap 80 on the distal end of the tubular port member 50, is deformed downwardly and inwardly and is subjected to an elevated temperature to effect a thermosetting of the material of the skirt 87 so that the skirt 87 takes on the permanent set in the configuration illustrated in FIGS. 2 and 3. The skirt 87 is sufficiently resilient to be temporarily deformed outwardly when the cap 80 is pulled off of the tubular port member 50. However, the skirt 87 returns to its inwardly curved orientation illustrated in FIG. 2 after the flange 85 of the cap 80 has been pulled past the skirt 87. If an attempt is subsequently made to re-install the cap 80 on the tubular port member 50, the cap flange 85 will engage the inwardly curved skirt 87 on the tubular port member 50, and this engagement will prevent the cap 80 from being fully installed on the tubular port member 50. This serves a tamper-indicating function to indicate that the cap 80 has been pulled outwardly at least far enough to move the cap flange 85 beyond the skirt 87.

As shown in FIG. 2, the tubular port member 50 includes three, internal, annular formations: (1) a lower or distal formation, such as first bead or ring 57 with an inner frustoconical surface 57' and an outer frustoconical surface 57", (2) an intermediate or second formation, such as a second bead or ring 58, and (3) a third or proximal formation, such as an upper or third ring or shoulder defining a frustoconical surface 59. These formations function as constraint features or guide features for the penetrator element 60 as described in more detail hereinafter.

In some prior art flexible containers, a pierceable diaphragm element is located near the lower or bottom open end of the port assembly. However, in the port system of the present invention, the diaphragm 55 is located at the upper, or proximal, inlet end 52 of the port system. Although there is an ISO standard for piercing pins, there are various dimensional variations among known piercing pins. Thus, the port assembly 12 of the present invention includes the penetrator element 60 as a dedicated piercing mechanism which functions as a universal piercing pin adapter for most of the known pins. The element 60 is adapted to be slide upwardly in the tubular member 50 as described hereinafter.

The penetrator element 60 is generally cylindrical and is slidably contained within the tubular port member 50. The penetrator element 60 is preferably molded from material such as high density polyethylene, for example, and has a beveled end 62. The end 62 is adapted to shear or puncture the container film diaphragm 55 and penetrate the sealed inner chamber 14 of the container.

The upper, shearing or puncturing end of the penetrator element 60 has a hollow chamber 64 opening forwardly onto the face of the beveled end 62. This chamber 64 functions as, or defines, a first fluid passageway into the penetrator element 60. The bottom end of chamber 64 opens to a larger, second passageway 66 which extends to an opposite, lower open end 70. A flow channel 69 is defined in the wall of the element 60 and communicates radially with the hollow chamber 64. The channel 69, chamber 64, and passageway 66 define a flow passage for providing fluid communication from the end 62 of the penetrator element 60 to the access fitment 51 of the port member 50.

Finally, the exterior, lower surface of the penetrator element 60 defines an annular, frustoconical shoulder 71. The shoulder 71 limits the upward sliding movement of the element 60 as described in detail hereinafter.

As shown in FIGS. 2 and 3, the second end 70 of the penetrator 60 is adaptable to any conventional piercing pin configuration.

FIGS. 7–11 illustrate the insertion of a conventional piercing pin 90 into the port member 50 to puncture the diaphragm 55. A length of administration tubing (not shown) is typically attached (by known, conventional means) to the bottom of the piercing pin 90. The tubing carries the liquid from the container 10 to the patient or administration device. Before insertion of the pin 90, the penetrator element 60 is in a retracted position (FIGS. 2 and 3) with the lower end 70 adjacent or engaging the frustoconical surface 57' of the constraining ring 57. The cover member 80 must be removed so that the pin 90 can be inserted.

Figure 11:
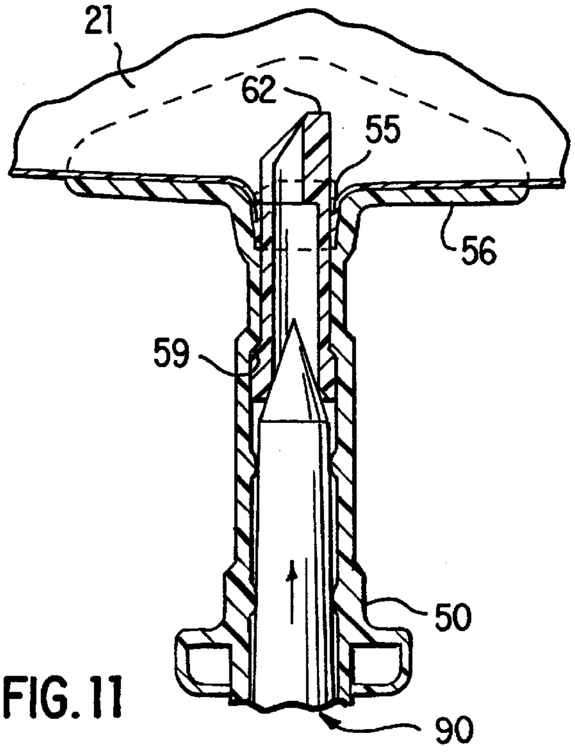
FIG. 11 is a fragmentary, cross-sectional view taken generally along the plane 11—11 in FIG. 10.
Figure 10:
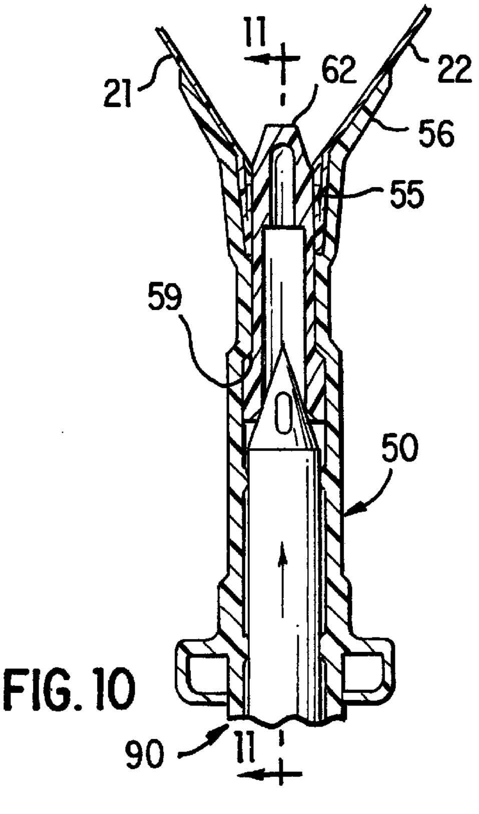
FIG. 10 is a view similar to FIG. 8, but FIG. 10 shows the piercing pin urging the penetrator element to the fully advanced position wherein the container film diaphragm has been pierced.

The conical, distal end of the pin 90 enters the bottom, open end 70 of the penetrator 60 until engagement is established (FIGS. 6 and 7). Continued advancement of the pin 90 pushes the penetrator element 60 up against the diaphragm 55. The diaphragm 55 is initially stretched (FIGS. 8 and 9) and is ultimately sheared and penetrated (FIGS. 10 and 11). The penetrator element 60 continues to be pushed up through the diaphragm until the penetrator element shoulder 71 engages the port member shoulder 59 (FIGS. 10 and 11). In the fully advanced position, the upper, beveled end 62 of the penetrator element preferably does not extend beyond the top edges of the walls of the saddle 56.

The fluid port member saddle 56, along with the sump 30 on the bottom surface of the flexible container 10 and along with the flow passageways 64, 66, and 69 in the penetrator 60, accommodate complete draining of the container. This prevents residual solution from remaining in the bottom of the flexible container 10.

FIGS. 7–11 show a conventional piercing pin 90 received in the tubular member 50. Any suitable conventional or special piercing pin 90 may be employed. Although the illustrated pin 90 is shown with one conventional configuration, there are a wide variety of lengths or "effective" lengths of conventional piercing pins (relative to the length of the penetrator element 60). There are some conventional pins which are relatively short. The port assembly 12 of the present invention allows even these short pins to advance the penetrator element 60 sufficiently to still effectively pierce the diaphragm 55 without requiring an excessively long penetrator element 60 which might otherwise extend beyond the saddle 56 and damage (i.e., rupture) the upper sidewall of the flexible container 10.

The penetrator element slot or channel 69 allows complete drainage through the penetrator element as the liquid level in the container falls below the open, beveled end 62 of the penetrator element 60. The use of a V-shaped saddle 56 tends to form the bottom of the container into a configuration which enhances the drainage capability of the container.

The location of the film diaphragm 55—recessed within the port assembly 12—can effectively accommodate a variety of piercing pins, including relatively short piercing pins. The recessed location of the diaphragm 55 within the port assembly 12 allows for earlier penetration of the film by the penetrator element 60 and lessens the risk of sidewall puncture. However, owing to the seal between the film 82 and shoulder 53, and owing to the frustoconical configuration of the sump 30 inside the tubular port member 50, the container film 82 is protected from being pierced at any location other than at the diaphragm 55—even when long piercing pins 90 are employed. The recessed location of the film diaphragm 55 in the body of the port member 50 results in a controllable weakening of the film which allows earlier penetration of the diaphragm 55 and thus accommodates a wide variety of piercing pin lengths.

A process for fabricating a sterile formed, filled, and sealed container 10 will now be described with reference again to FIG. 12. A continuous, longitudinal strip of multiple layer film or sheet 82 is provided in a roll 84. The film is unwound and sterilized in a predetermined, continuous indexing movement.

The sterilized film or sheet 82 is continuously indexed and longitudinally moved in a roller assembly through a sterile core environment 23 of the packaging line. With the sheet 82 in a generally flat orientation, the port assemblies 12 are attached along the saddle line or center portion of the continuous sheet 82 at a station P. The flat sheet 82 runs downwardly at an angle in the station P. In the station P, each tubular port assembly 12 is preferably attached to the outside surface of the film 82 by thermal bonding with a heated die that simultaneously causes the sheet 82 to form the fluid sump 30 and establish an annular circumferential seal around the orifice of the open end 52 of the tubular port member. Preferably, the relevant portion of the film is heated, and the saddle 56 of the port member 50 is heated so that a circumferential bond or seal is created around the saddle 56 by means of a thermal bonding process. This can include the use of a sealing die which moves downwardly to force the film 82 against the seal shoulder 53 of the tubular port member 50 to form the sump 30 and to effect the seal of the periphery of the diaphragm 55 to the shoulder 53. The film above the diaphragm 55 is also sealed to the frustoconical surface above the shoulder 53, and to the V-shaped walls of the saddle 56. Alternatively, other bonding processes could be used.

In a preferred form of the fabrication process, the side portions of the film 82 are formed or plowed into a continuous trough with a rounded bottom so as to define the sidewalls of the container extending up from the bottom surface 40 (FIG. 4). The opposed sides or layers 21 and 22 of the film 82 are sealed together with the first transverse side seal 42 (FIG. 1) that extends from the bottom surface 40 to the outer, upper edge of the film. As the continuous indexing film advances through the packaging machine 20, a second portion of the opposed layers or sides 21 and 22 of the film is sealed together to form the second, parallel, transverse side seal 44 extending from the bottom surface 40 to the top, upper edge. The first side seal 42, the bottom surface 40, and the second side seal 44 define an open pouch.

As the pouch is advanced along the packaging line in the filtered sterile air of the sterile core environment, it may optionally be flushed with a flushing agent (at a flushing station, the beginning of which is schematically represented in FIG. 12 with the letter A). The agent may be a suitable gas such as nitrogen. The flushing agent removes substantially all of the air from the pouch pocket.

Subsequently, a sterile solution liquid is metered through a filling nozzle D into the pouch and displaces the flushing agent or sterile air.

After the pouch is filled with the metered sterile solution, a third portion of the film sides 21 and 22 along the top of the pouch is sealed together to form the top seal 46. This creates hermetically sealed, flexible containers which contain the sterile solution. At this point in the process, the continuous strip of filled, flexible containers exit the sterile core environment. Preferably, the strip of containers is cut coincident with (i.e., vertically through) the first and second side seals 42 and 44 (FIG. 1), respectively, so as to divide the continuously formed, filled, and sealed film into individual, sealed containers 10. Although this cutting step may be performed inside the sterile core environment 23, it is preferable to perform cutting outside the core environment 23 so that the scrap or particulate will not accumulate in the sterile core environment 23.

Because all of the individual components, namely, the film 82, the port assembly 12, and the sterile solution, have been separately sterilized and are brought together in the sterile core environment 23, there is no need for further sterilization, such as terminal sterilization. This allows heat-sensitive drugs, for example, to be pre-sterilized and packaged in flexible containers without degradation of the solution due to overheating during a traditional terminal sterilization process (such as autoclaving).

Because the diaphragm 55 of the port assembly 12 includes the flexible film 82, there is no region of different, higher permeability in the attached port system 12 such as encountered in some previously known flexible containers with ports. Thus, there is no need to use an overwrap material for the flexible container and port assembly of the present invention, nor is there a need for a terminal sterilization process. This invention thus allows a wide variety of sensitive drugs and other solutions, especially oxygen-sensitive drugs, to be packaged in a formed, filled, and sealed flexible container.

Figure 21:
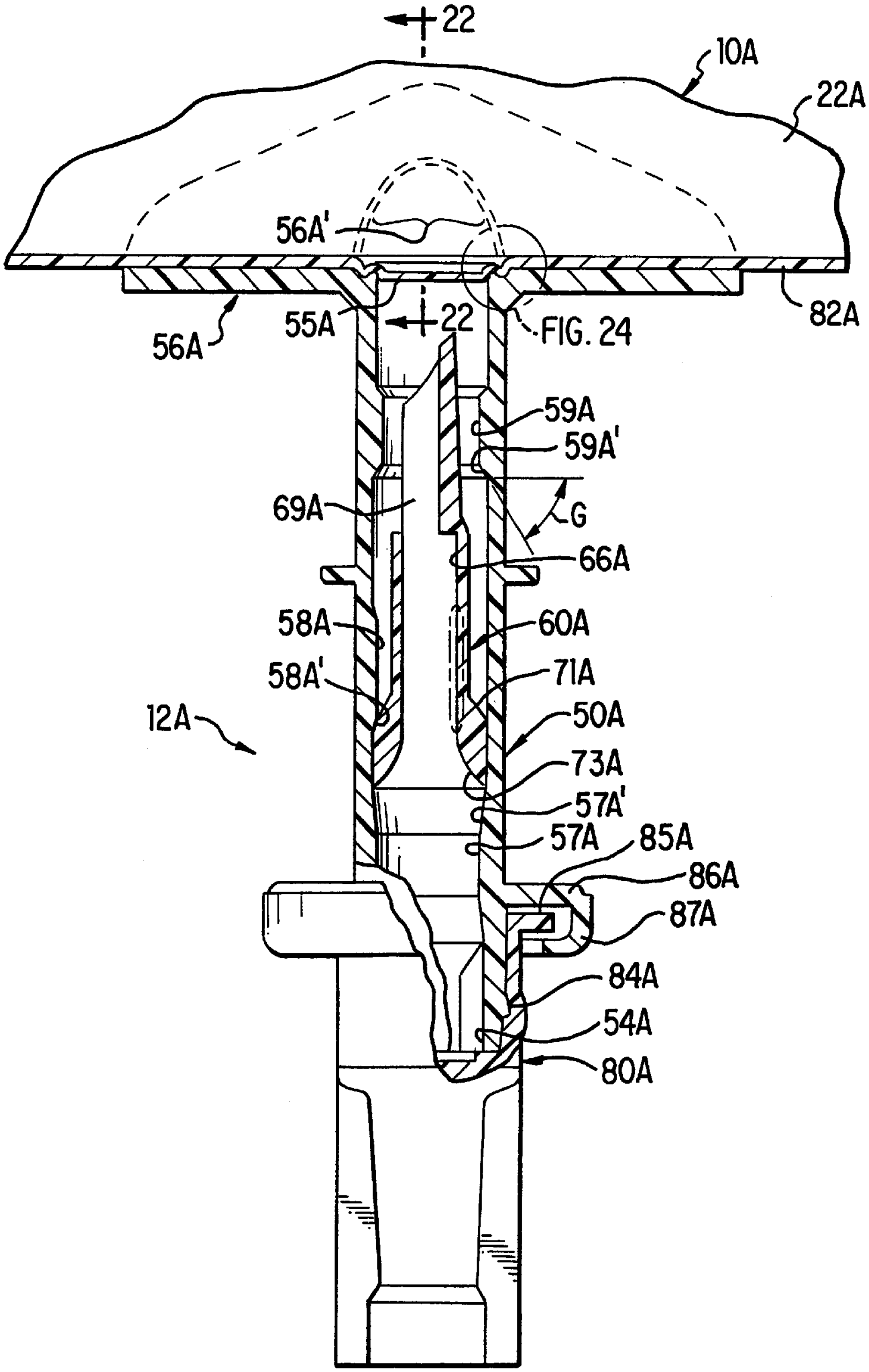
FIG. 21 is a fragmentary, cross-sectional view similar to FIG. 17, but FIG. 21 shows (1) the tubular port member sealed to a flexible container, (2) a penetrator element in the tubular port member, and (3) a cap or cover on the lower, discharge end of the tubular port member.
Figure 22:
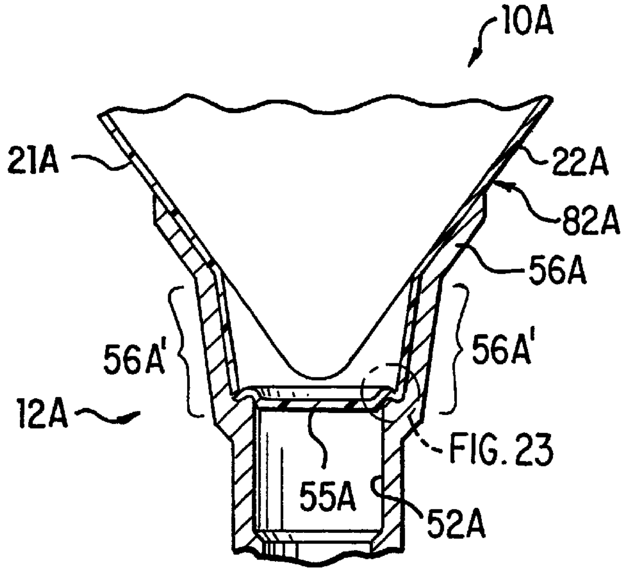
FIG. 22 is a fragmentary, cross-sectional view taken generally along the plane 22—22 in FIG. 21.

Referring now to FIGS. 13–30, a second embodiment of the port assembly is illustrated and is designated in FIGS. 13–17, 21, and 29–30 with the reference number 12A. As shown in FIG. 21, the port assembly 12A includes a tubular port member 50A projecting from a saddle 56A, a cylindrical penetrator element 60A, and a cap or cover member 80A. As with the first embodiment saddle 56 illustrated in FIGS. 1–12 and described above, the second embodiment saddle 56A is adapted to be heat-sealed or thermally bonded to the outer surface of a container, such as the container 10A (FIG. 21). The container 10A may have the generally same basic structure as the container 10 described above with reference to FIGS. 1–12. The container 10A is preferably formed from a folded sheet of film 82A to define sides 21A and 22A (FIG. 22).

Figure 17:
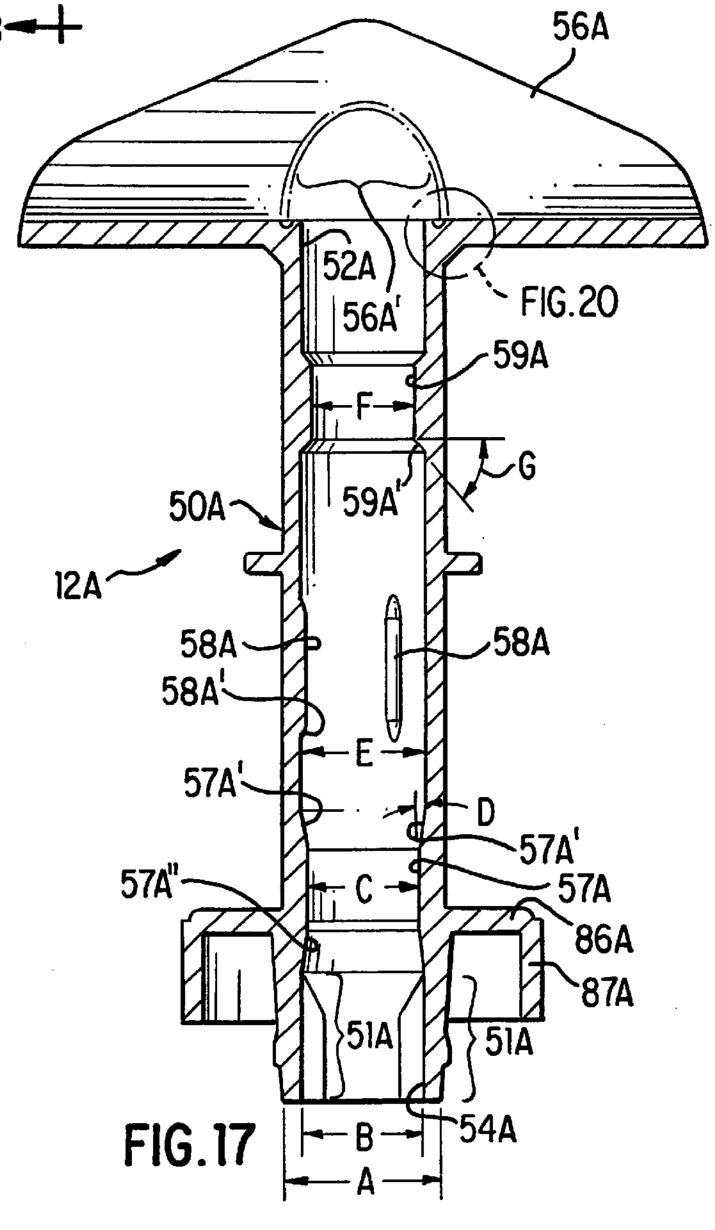
FIG. 17 is a cross-sectional view taken along the plane 17—17 in FIG. 16.

As shown in FIG. 17, the tubular port member 50A has a proximal, inlet end 52A merging with the saddle 56A and has a distal, discharge end 54A which is occluded by the cap 80A (FIG. 21) until just prior to use.

The member 50A is preferably molded from a heat-bondable, medical grade thermoplastic. Preferably, the port member 50A is either molded from the same material as, or is at least compatible with, and bondable to, the outer surface of the film 82A. In one contemplated embodiment, the tubular port member 50A is preferably injection molded from an olefin, for example, a linear low density polyethylene such as sold in the U.S.A. under the trade name Dowlex 3010.

Figure 13:
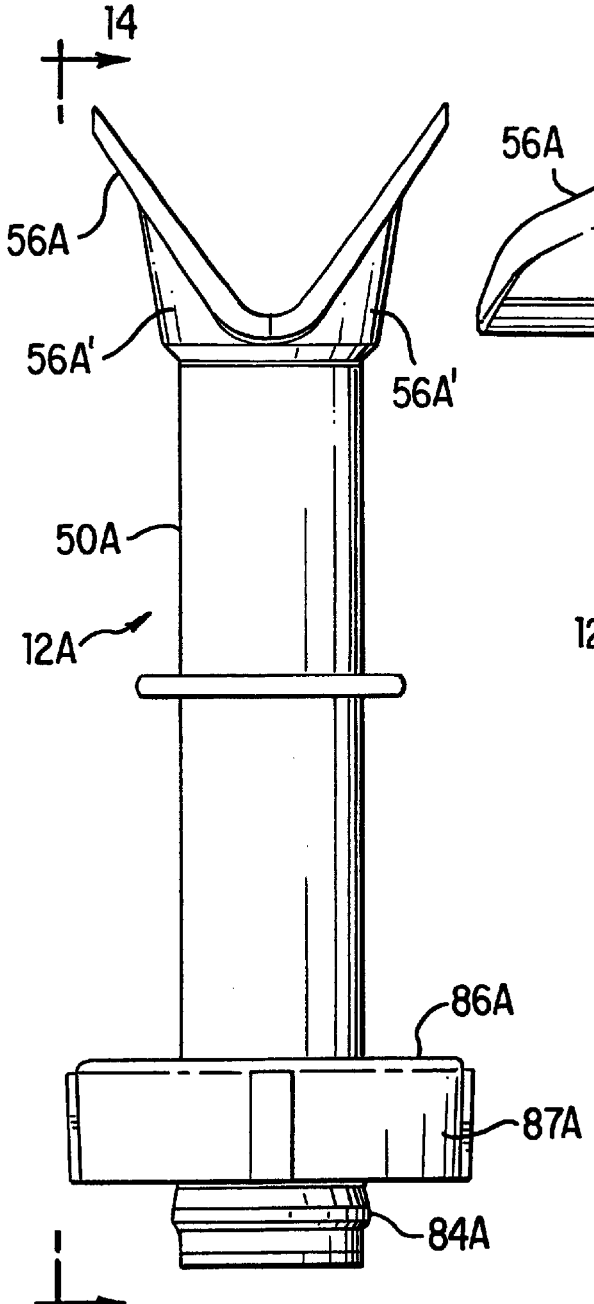
FIG. 13 is a greatly enlarged, side elevational view of a second embodiment of the tubular port member of the present invention prior to installation of a penetrator element and end cap.
Figure 14:
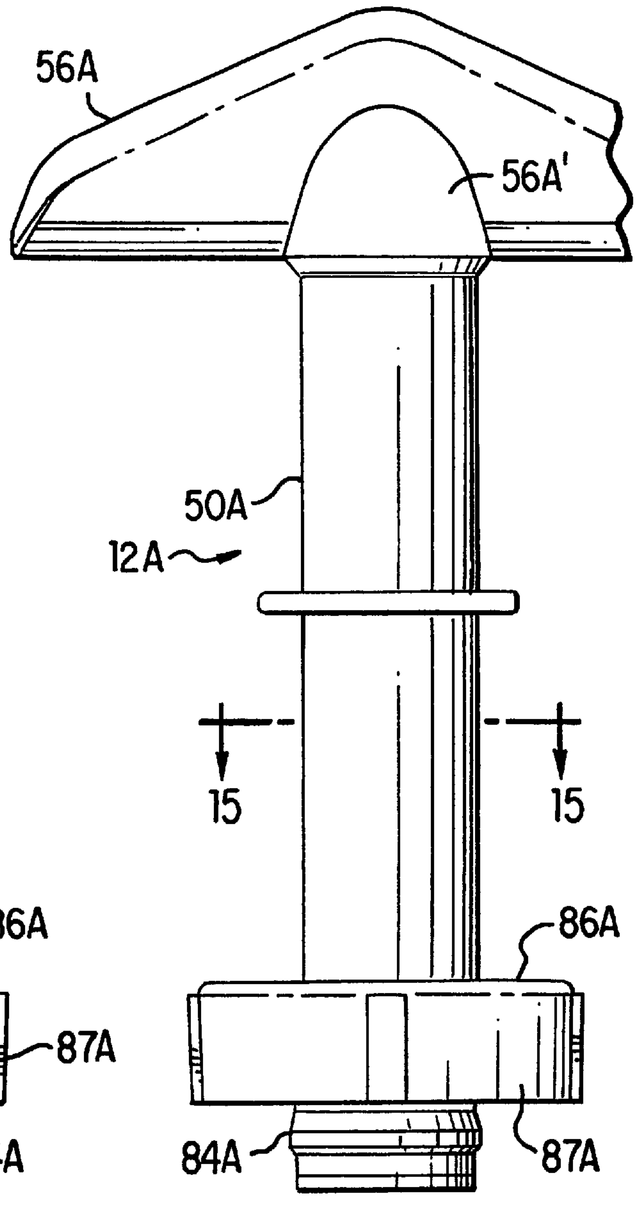
FIG. 14 is a front elevational view taken generally along the plane 14—14 in FIG. 13.
Figure 18:
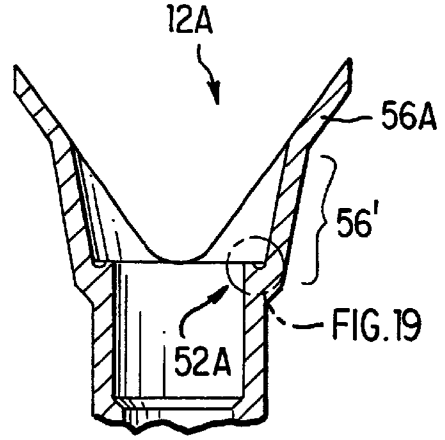
FIG. 18 is a cross-sectional view taken generally along the plane 18—18 in FIG. 16.

The tubular port member 50A may be characterized as including the integral saddle or flange 56A that surrounds the proximal, inlet end 52A. The saddle or flange 56A is preferably V-shaped in cross section (FIGS. 13 and 18). In the preferred embodiment, the interior, diverging, planar regions of the saddle 56A define an included angle of about 70.4 degrees.

The tubular port member 50A has a shoulder region at the proximal, inlet end 52A which has a pre-installation configuration (FIGS. 18–20) that differs from the post-installation configuration (FIGS. 21–24) after the film 82A has been sealed to the port member 50A. In the as-molded, pre-installation configuration, the inlet end 52A of the tubular member 50A defines an inner circular annulus functioning as an annular sealing shoulder 53A (FIGS. 19 and 20) which will be subsequently deformed and sealed to a portion of the film 82A.

The shoulder 53A includes at least (1) a radially inner, generally planar, annular first surface 53A', and (2) a radially outer, generally arcuate, annular second surface 53A" extending from the first surface 53A'. The second surface 53A" has a transverse cross section which in part defines an arc of a circle. The second surface 53A" thus defines an annular groove for receiving a portion of the film 82A to be heat-sealed thereto in conformity therewith.

Figure 19:
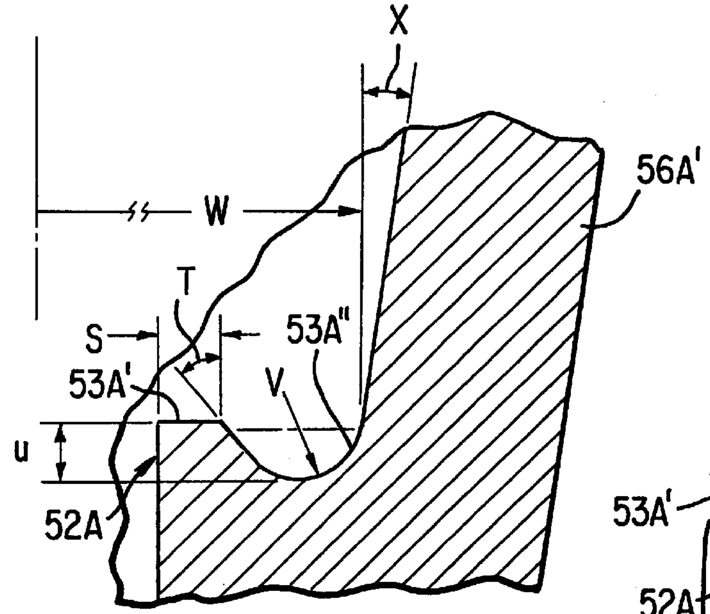
FIG. 19 is an enlarged, fragmentary view taken generally within the circle designated FIG. 19 in FIG. 18.
Figure 20:
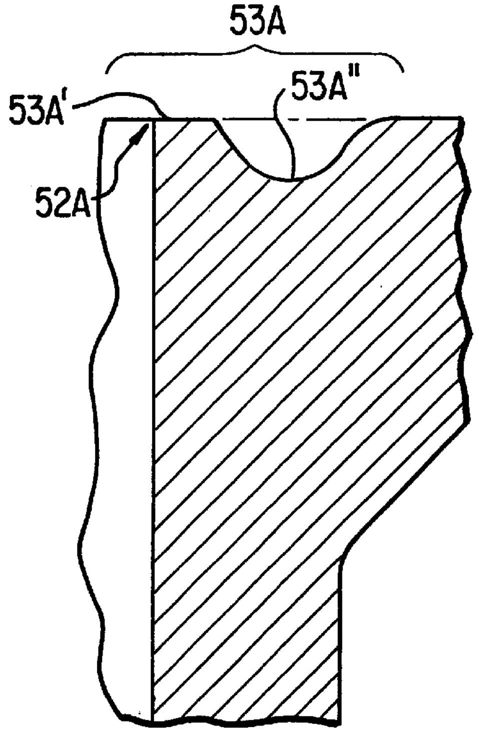
FIG. 20 is an enlarged, fragmentary view taken generally within the circle designated FIG. 20 in FIG. 17.

In a preferred form of the shoulder 53A as illustrated in FIG. 19, the first surface 53A' has an annular width S of about 0.01 inch. The second surface 53A" defines a part of an arc of a circle at the bottom of the groove and extends upwardly from the circular arc in a straight line to the first surface 53A' at an angle T which is preferably about 38 degrees. The depth of the groove (i.e., the vertical distance between first surface 53A' and the bottom of the groove at the second surface 53A") is preferably 0.01 inch. This is indicated by the dimension U in FIG. 19. The radius of the circular arc at the bottom of the groove defined by the second surface 53A" is indicated by the radius dimension V in FIG. 19 and is preferably about 0.01 inch. The outer end of the circular arc defining the bottom of the groove of the second surface 53A" is located at a distance W radially outwardly from the longitudinal centerline of the tubular port member 50A, and in the preferred embodiment, the distance W is about 0.138 inch. The saddle 56A extends upwardly from the outer end of the circular arc surface at an angle X as shown in FIG. 19, and the angle X is preferably about 9.4 degrees.

Figure 23:
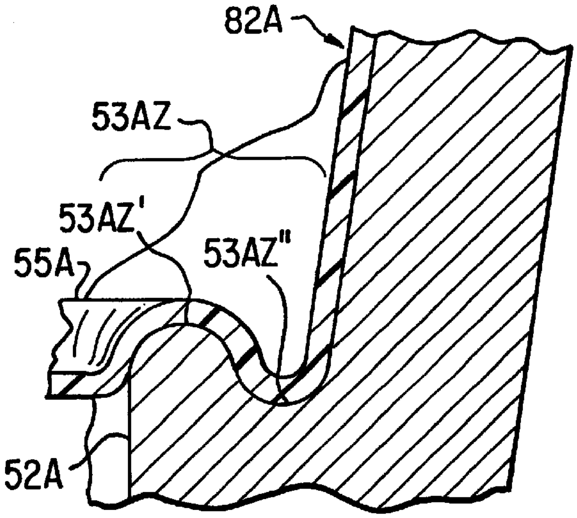
FIG. 23 is an enlarged, fragmentary view taken generally within the circle designated FIG. 23 in FIB. 22.
Figure 24:
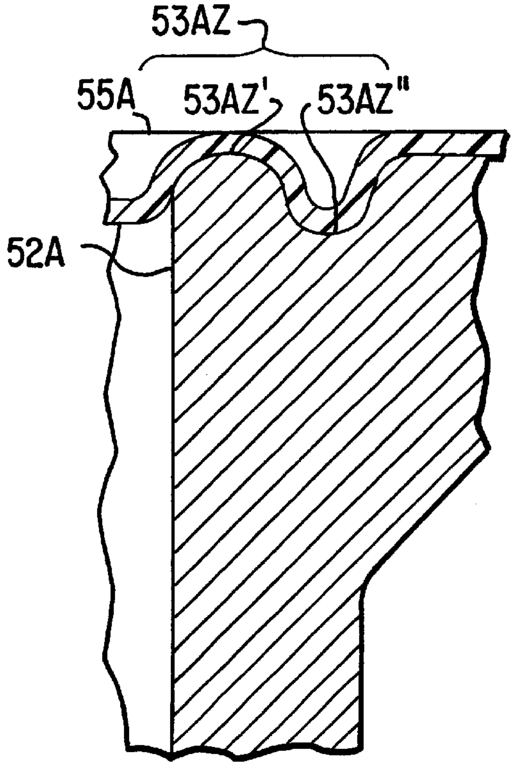
FIG. 24 is an enlarged, fragmentary view taken generally within the circle designated FIG. 24 in FIG. 21.
Figure 26:
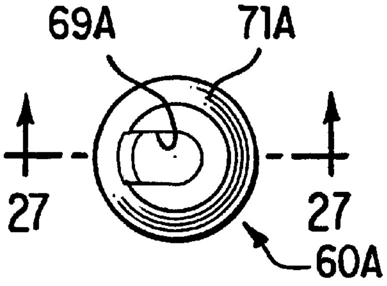
FIG. 26 is a top plan view of the penetrator element shown in FIG. 25.
Figure 25:
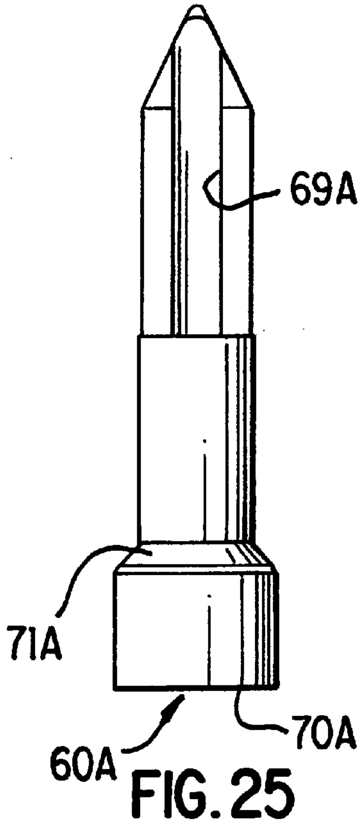
FIG. 25 is a front, elevational view of the penetrator element prior to installation in the tubular port member shown in FIGS. 13–20.

During assembly of the film 82A to the port assembly 12A, a heated die (not illustrated) presses the film 82A into the tubular port member saddle 56A to form a diaphragm 55A and seal the film 82A at the periphery of the diaphragm 55A to port member 50A. As shown in FIG. 22, the contoured saddle 56A is sealed to the film sides 21A and 22A around the proximal inlet end 52A of the tubular port member 50A so that there is an annular (i.e., circumferential) fluid seal around a central portion of the film 82A which defines the diaphragm 55A. The sealing force deforms the annular shoulder 53A' (FIGS. 19 and 20) to the rounded shape 53AZ' as shown in FIGS. 23 and 24. Further, the force of the die acting on the groove in the surface 53A" (FIGS. 19 and 20) increases the depth (FIGS. 23 and 24 show a deeper groove 53AZ").

Preferably, the film 82A is heat-sealed or thermally bonded to the shoulder 53A' (FIGS. 19 and 20) using a heat seal die (not illustrated) that matches the features of the final configuration shown in FIGS. 23 and 24. This heat-sealing process also stretches the film 82A, and this weakens the film 82A somewhat at the diaphragm 55A. Subsequently, when the penetrator element 60A is advanced to puncture the diaphragm 55A, the diaphragm 55A preferentially tears at and along the contact point as the penetrator element 60A advances through the film defining the diaphragm 55A. The heat seal or thermal bond at the periphery of the diaphragm 55A between the film 82A and the port assembly shoulder 53A is relatively strong and prevents the film 82A from being pulled away from the sealing shoulder 53A. The force required to pierce the diaphragm 55A is significantly less than the force required to separate the film 82A from the shoulder 53A. The strength of the heat seal attachment between the film 82A and the port assembly shoulder 53A, in the preferred embodiment, exceeds 30 pounds average tension force. In tests of actual specimens, the tension force at failure (i.e., separation of the film 82A from the shoulder 53A) exceeded 40 pounds average tension.

In a preferred process for heat-sealing the film 82A to the shoulder 53A, a teflon-coated heat seal die is employed at operating temperatures of about 385° F. for a die contact time of between 1 and 2 seconds for preferred multilayer films. The detailed design and operation of the particular sealing die form no part of the present invention.

The film is preferably a multilayer film in which the two outer layers are of the same material which can each be heat-sealed to itself and also to the port assembly 12A (FIG. 13) where the port assembly is molded from linear low density polyethylene (e.g., the material sold under the designation or trade name Dowlex 3010). The multilayer film preferably provides a relatively high barrier to oxygen and moisture transmission (i.e., permeation), is resistant to high temperatures, and can bond to non-compatible port assembly materials. As described below, the multilayer film includes a layer (such as Saran) which provides a high barrier to oxygen and moisture and is resistant to high temperatures. This barrier layer by itself cannot bond to the "non-compatible" port assembly materials. The combination of layers of the film however allows the film (including the barrier) to bond to such port assembly materials.

The multilayer film preferably includes conventional tie layers, such as conventional polyolefin copolymers well known to those skilled in the art. One suitable multilayer film comprises an exterior layer of linear low density polyethylene about 2.5 mils thick, a tie layer about 0.2 mils thick, a layer of Saran about 1.1 mils thick, a tie layer about 0.5 mils thick, a layer of ethylene vinyl alcohol about 1.0 mils thick, a tie layer about 0.3 mils thick, a low density polyethylene layer about 0.5 mils thick, a linear low density polyethylene layer about 0.3 mils thick, a tie layer about 0.3 mils thick, a layer of nylon about 0.6 mils thick, a tie layer about 0.3 mils thick, and an exterior layer of linear low density polyethylene about 1.5 mils thick. The overall thickness of the multilayer film is nominally 9.1 mils and is preferably in the range from about 8.2 mils to about 10.0 mils.

Another suitable multilayer film comprises an exterior layer of linear low density polyethylene about 1.8 mils thick, a tie layer about 0.2 mils thick, a layer of Saran about 1.1 mils thick, a tie layer about 0.2 mils thick, a layer of linear low density polyethylene about 0.7 mils thick, a low density polyethylene layer about 0.5 mils thick, a linear low density polyethylene layer about 0.3 mils thick, a tie layer about 0.3 mils thick, a layer of nylon about 0.6 mils thick, a tie layer about 0.3 mils thick, and an exterior layer of linear low density polyethylene about 1.5 mils thick. The overall thickness of the multilayer film is nominally 7.5 mils and is preferably in the range from about 6.8 mils to about 8.2 mils.

The V-flange shape of the saddle 56A functions especially well to receive and hold the flexible container film 82A. The saddle 56A accommodates heat sealing of the interior of the saddle to the exterior surface of the flexible container film 82A so as to provide a very good bond. At least the lowest portions of the saddle 56A are preferably provided with a substantially uniform or constant wall thickness so that quality control testing and measurement of the seal thickness can be readily made.

A partially cone-shaped cavity at the center of the saddle 56A may be characterized as a "formed diaphragm area." The formed diaphragm area is defined by the intersection V-shaped portions of the saddle 56A and the round port tube. As shown in FIG. 22, the lower, central portions of the saddle 56A taper slightly outwardly as illustrated in the regions designated by the brackets 56A'. The portions 56A' define partially frustoconical regions, and the upper edges of the portions 56A' merge with generally planar portions of the saddle or flange 56A. This design effectively provides a transition between the port assembly 12A and the generally two-dimensional shape of the walls 21A and 22A of the flexible container 10A. This also provides an ergonomic grip for holding the port assembly 12A during insertion of a piercing pin (described hereinafter).

During the heat-sealing process, the bag film is sealed simultaneously to the annular shoulder 53A around the diaphragm and to the sidewalls of the saddle 56A. This provides a package combination with a high-integrity seal which functions as intended during piercing of the diaphragm 55A with the penetrator element 60A.

It will also be appreciated because the diaphragm 55A is formed from the film 82A of the flexible container, rather than from a separate material, the expense and complexity of the diaphragm design is minimized. Further, when the material used for the flexible container film 82A has good oxygen barrier properties, or good barrier properties with respect to other gases, the diaphragm 55A will itself necessarily provide such gas barrier properties. Thus, there will be no loss of gas barrier properties compared to use of a separate diaphragm material that does not have such good gas barrier properties.

Figure 29:
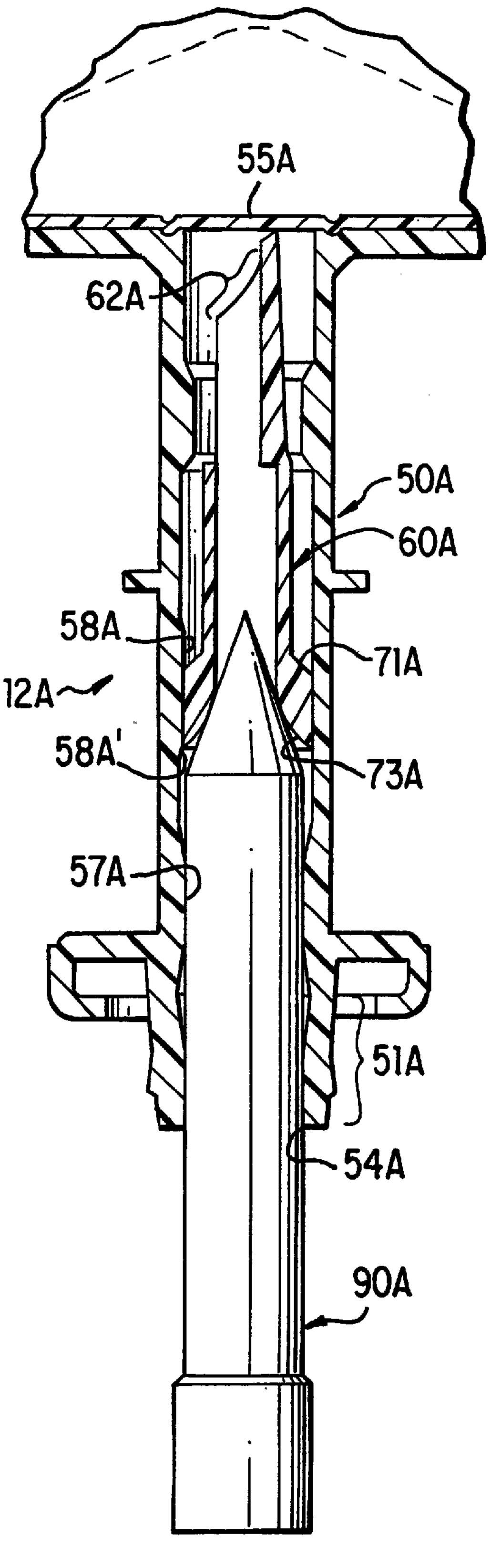
FIG. 29 is a view similar to FIG. 21, but FIG. 29 shows a conventional piercing pin inserted into the tubular port member to move a penetrator element toward a fully advanced position.
Figure 30:
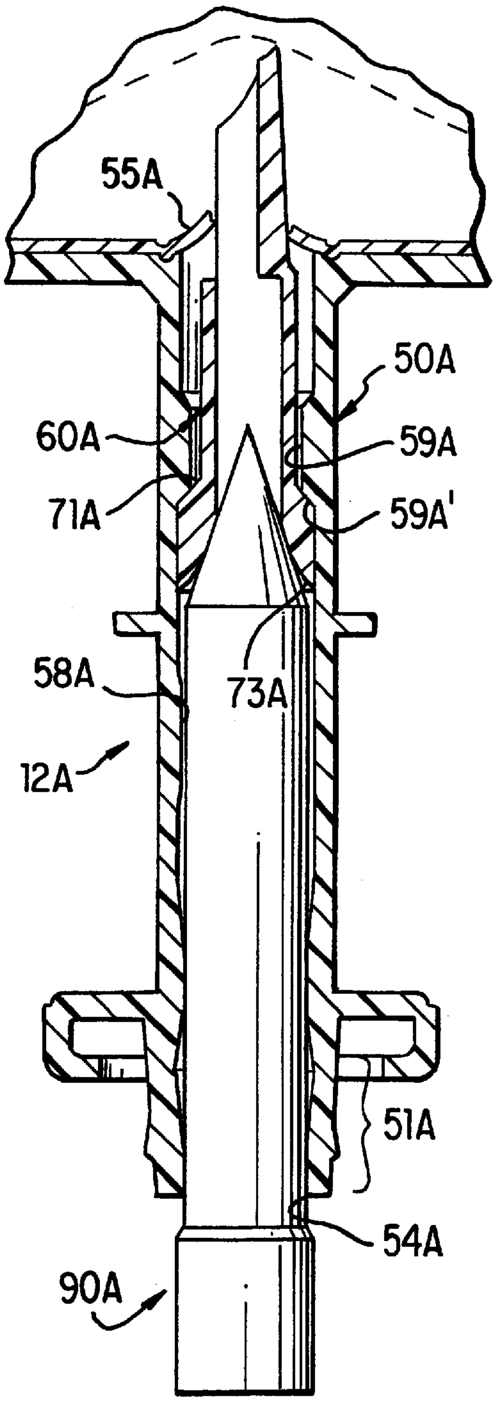
FIG. 30 is a view similar to FIG. 29, but FIG. 30 shows the piercing pin urging the penetrator element to the fully advanced position wherein the container film diaphragm has been pierced.

The distal, discharge end 54A of the tubular port member 50A includes an administration fitment or access fitment 51A (FIGS. 17, 29, and 30) that is fluid tight when connected with conventional medical fluid connectors, such as a piercing pin 90A (FIGS. 29 and 30). As shown in FIG. 17, the diameter A at the outlet of the discharge end of the fitment 51A has a slightly smaller diameter than the inner portion of the fitment 51A. The interior surface of the fitment 51A tapers from a larger diameter B to the smaller diameter A. In a preferred embodiment, the outlet diameter A is about 0.200 inch and the inner diameter B is about 0.210 inch. The reduced diameter A at the outlet accommodates piercing pins 90 of varying diameters. The reduced diameter A insures shut-off or sealing around the pin 90 before the container diaphragm 55A (FIG. 21) is pierced.

The tubular port member 50A is initially covered or occluded with a removable cover or cap 80A (FIG. 21). The cap maintains sterility of the tubular port member opening at the discharge end 54A. The cover 80 is preferably made from an injection molded material or from a compression set, resilient, elastomeric material. As shown in FIG. 21, the cover 80A is preferably sufficiently resilient to effect a frictional engagement with an annular bead 84A on the port member 50A.

The inner end of the cover or cap 80A includes a peripheral flange 85A, and the tubular port member 50A includes a flange 86A with an extending skirt 87A. This configuration of flanges is identical with the configuration of flanges in the first embodiment of the port assembly described above with reference to FIGS. 1–12. The tubular port member 50A is initially molded with the flange 86A and skirt 87A extending radially therefrom. After the cap 80A is fully inserted on the distal end of the tubular port member 50A, the skirt 87A is deformed downwardly and under the cap flange 85A and is subjected to heat so as to effect a permanent set of the skirt 87A. Thus, as the cap 80A is removed, the skirt 87A is temporarily deformed outwardly as the cap flange 85A moves past the skirt 87A. The skirt 87A then returns to the inwardly curved configuration. Thus, if an attempt is made to re-install the cap 80A, the cap flange 85A will engage the lower, bottom surface of the skirt 87A, and this interference will prevent the cap 80A from being fully installed on the tubular port member 50A. Thus, the frictional engagement between the cap 80 and the bead 84A cannot be established. This provides a tamper-indicating function and alerts the user that the cap 80A has been pulled outwardly from the initial, fully installed position.

The tubular port member 50A includes a number of internal formations. As illustrated in FIG. 17, the tubular port member 50A includes an internal, proximal formation 59A defining a frustoconical surface 59A' serving as an abutment shoulder against which a portion of the penetrator element 60A abuts when the penetrator element 60A is in a fully advanced position (FIG. 30) within the tubular port member 50A. The frustoconical surface 59A', as illustrated in FIG. 17, defines an angle G relative to a plane that is normal to the longitudinal axis of the tubular port member 50A. The angle G is about 50 degrees.

The proximal formation 59A also defines a short, cylindrical region having a diameter F. In a preferred embodiment, the diameter F is about 0.175 inch.

The tubular port member 50A includes an internal, distal formation 57A defining a frustoconical surface 57A' forming an abutment shoulder which is engaged by a portion of the penetrator element 60A when the penetrator element 60A is in a fully retracted position (FIG. 21). The frustoconical surface 57A' defines an angle D (FIG. 17) of about 7.5 degrees relative to the longitudinal axis of the tubular port member 50A. The internal, distal formation 57A also defines a short, cylindrical region having a diameter C (FIG. 17) which serves to guide and center conventional piercing pins, such as the conventional piercing pin 90A (FIGS. 29 and 30). The diameter C is about 0.190 inch.

Figure 15:
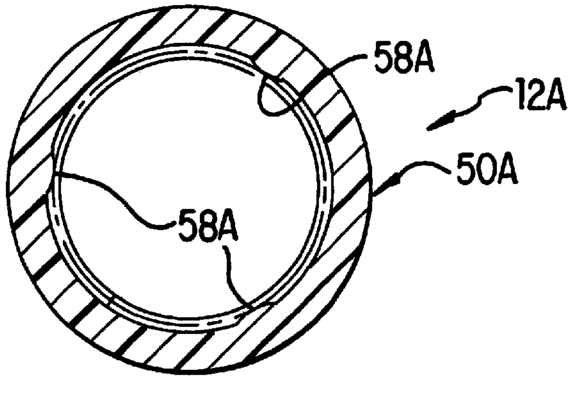
FIG. 15 is a cross-sectional view taken generally along the plane 15—15 in FIG. 14.
Figure 16:
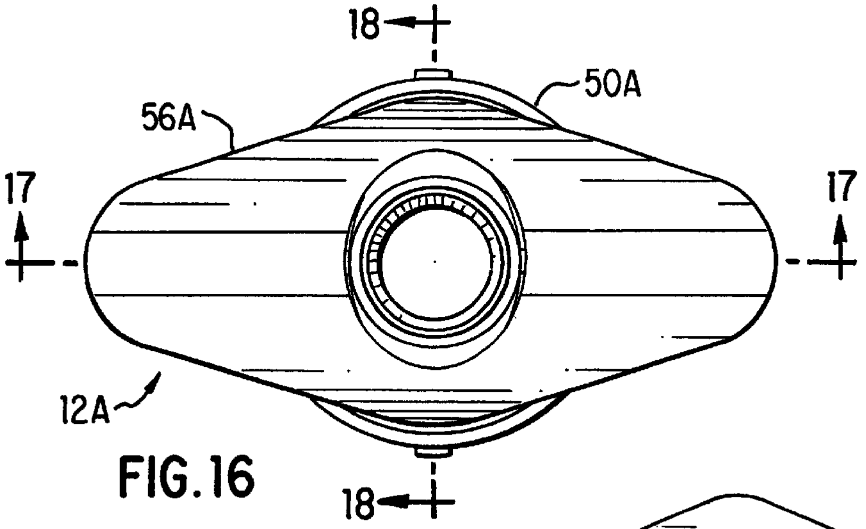
FIG. 16 is a top plan view of the second embodiment of the tubular port member.

The tubular port member 50A also has an internal, intermediate formation which includes three, circumferentially spaced ribs 58A (FIGS. 17 and 15). The ribs 58A project radially inwardly from the interior surface of the tubular port member 50A. The interior surface of the tubular port member in the region of the ribs 58A is generally cylindrical and has a diameter E. In the second embodiment illustrated in FIG. 17, the diameter E is about 0.210 inch. The ribs 58A serve to retain the penetrator element 60A centered in the desired position in the tubular port member 50A and prevent the penetrator element 60A from inadvertently sliding forwardly toward the diaphragm 55A. To this end, the lower end of each rib 58A includes an angled surface 58A' (FIG. 21). The rib surface 58A' engage a surface on the penetrator element 60A when the penetrator element 60A is in the fully retracted position.

It will be appreciated that the reduced diameter opening at the distal, discharge end 54A of the tubular port member 50A and the reduced diameter distal formation 57A function as seals for sealing the various piercing pins (e.g., piercing pin 90A in FIGS. 29 and 30) which may have varying lengths and slightly varying diameters at these locations within the tubular member. The sealing structures on the interior of the tubular port member 50A are designed, along with other features, to provide the desired insertion and withdrawal forces with respect to various types of piercing pins (e.g., piercing pin 90A illustrated in FIGS. 29 and 30). To this end, the length of the cylindrical surface defined by the formation 57A is preferably about 0.123 inch.

Figure 27:
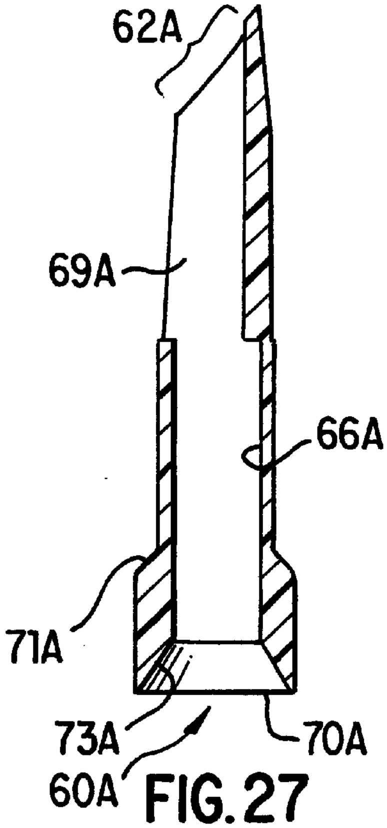
FIG. 27 is a cross-sectional view taken generally along the plane 27—27 in FIG. 26.
Figure 28:
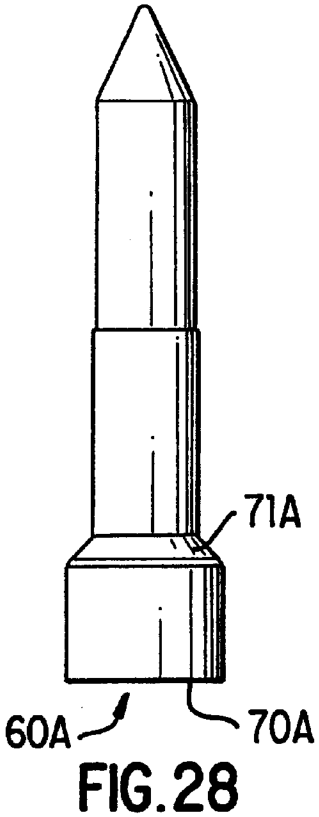
FIG. 28 is a rear elevational view of the penetrator element.

The second embodiment of the port assembly 12A includes the penetrator element 60A as a dedicated piercing mechanism which functions as a universal piercing pin adapter for most of the known pins. The penetrator element 60A (FIGS. 25–28) is generally cylindrical and is slidably contained within the tubular port 50A. The penetrator element 60A is preferably molded from material such as high density polyethylene, for example, and has a beveled end 62A (FIG. 27). The end 62A is adapted to shear or puncture the container film diaphragm 55A and extend into the sealed inner chamber of the flexible container 10A.

The beveled, puncturing end 62A of the penetrator element 60A has a groove 69A opening forwardly onto the face of the beveled end 62A. The groove 69A functions as, or defines, a first fluid passageway into the penetrator element 60A. The bottom end of groove 69A opens to a larger, second passageway 66A (FIG. 27) which extends to an opposite, lower open end 70A. The channel 69A and passageway 66A together define a flow passage for providing fluid communication from the end 62A of the penetrator element 60A to the access fitment 51A of the port member 50A. There is a frustoconical surface 73A on the interior of the penetrator element 60A at the bottom, outlet end 70A.

Finally, an exterior, lower surface of the penetrator element 60A defines an annular, frustoconical shoulder 71A. The shoulder 71A limits the upward sliding movement of the element 60A as described in detail hereinafter. The diameter of the bottom end of the penetrator element 60A is great enough to engage the tubular port member interior surface 57A' and prevent the penetrator element 60A from sliding further toward the distal end 54A of the tubular port member 50A. During the manufacture of the assembly 12A, the penetrator element 60A is initially forced into the distal end 54A of the tubular port member 50A with sufficient force to temporarily compress the shoulder 71A and/or temporarily expand the formation 57A in the tubular port member 50A so as to permit the penetrator element 60A to be properly position within the tubular port member 50A.

In the second embodiment illustrated in FIG. 17, the penetrator element 60A has a length of about 0.930 inch. The length of the channel 69A, between the top of the passage 66A and the uppermost, distal end of the penetrator element 60A, is about 0.455 inch. The length of the portion of the penetrator element containing the passage 66A is about 0.475 inch. The length of the base of the penetrator element 60A, from the outlet end 70A to the top of the frustoconical surface 71A, is about 0.193 inch. The angle of the frustoconical surface 71A relative to the vertical, longitudinal axis of the penetrator element 60A, is about 40 degrees. The outside diameter at the base of the penetrator element 50A at the bottom, outlet end 70A is about 0.210 inch. The outside diameter of the penetrator element 60A, above the frustoconical surface 71A and below the channel 69A, is about 0.15 inch. The internal diameter of the passage 66A is about 0.118 inch. The frustoconical surface 73A at the penetrator element outlet end 70A defines an angle of about 30 degrees relative to the vertical, longitudinal axis of the penetrator element 60A. The diameter of the upper portion of the penetrator element 60A which contains the channel 69A is about 0.138 inch. The vertical height of the beveled end 62A, as measured along the vertical, longitudinal axis of the penetrator element 60A, is about 0.150 inch.

As shown in FIGS. 29 and 30, the bottom end 70A of the penetrator 60A is adapted to engage various, conventional piercing pin configuration. FIGS. 29 and 30 illustrate the insertion of a conventional piercing pin 90A into the port member 50A to puncture the diaphragm 55A. Before insertion of the pin 90A, the penetrator element 60A is in a retracted position (FIG. 21) with the dispensing end shoulder 71A adjacent or abutting the lower ends 58A' of the ribs 58A. The cover member 80A must be removed so that the pin 90A can be inserted.

The pin 90A has a conical distal end which enters the bottom open end 70A of the penetrator 60A until engagement is established. Continued advancement of the pin 90A pushes the penetrator element 60A up toward the diaphragm 55A. The enlarged, lower portion of the penetrator element 60A is compressed and/or the tubular port member 50A expands as the penetrator element frustoconical surface 71A engages and slides along the ribs 58A.

As the penetrator element 60A moves forwardly, the beveled end 62A of the penetrator element 60A engages the film diaphragm 55A. The diaphragm 55A is initially stretched and is ultimately punctured (i.e., sheared, pierced, etc.) and penetrated by the beveled end 62A (FIGS. 10 and 11). The penetrator element 60A can continue to be pushed up through the diaphragm until the penetrator element shoulder 71A engages the port member shoulder 59A (FIG. 30). In the fully advanced position, the upper, beveled end 62A of the penetrator element 60A preferably does not extend beyond the top edges of the walls of the saddle 56*a*.

Although the illustrated pin 90A is shown with one conventional configuration, there are a wide variety of lengths or "effective" lengths of conventional piercing pins (relative to the length of the penetrator element 60A). There are some conventional pins which are relatively short. The second embodiment of the port assembly 12A may be used with conventional piercing pins shorter than the pin 90A illustrated in FIGS. 29 and 30. In such a situation, the penetrator element shoulder 71A may not engage the port member shoulder 59A', but the penetrator will still be advanced far enough to pierce the diaphragm 55A. The second embodiment of the port assembly 12A of the present invention allows even these short pins to advance the penetrator element 60A sufficiently to still effectively pierce the diaphragm 55A without requiring an excessively long penetrator element 60A which might otherwise extend beyond the saddle 56A and damage (i.e., rupture) the upper sidewall of the flexible container 10A.

The penetrator element slot or channel 69A allows drainage through the penetrator element as the liquid level in the container falls below the open, beveled end 62A of the penetrator element 60A.

The process for fabricating a sterile formed, filled, and sealed container 10A together with the port assembly 12A may be substantially the same as the process described above for the first embodiment illustrated in FIGS. 1–12 except that with the second embodiment there is no formation of a sump (e.g., sump 30 in FIGS. 5 and 12) and a differently shaped heat sealing die is used to seal the container film 82A to the annular shoulder 53A.

The second embodiment of the port assembly 12A will function properly with an ISO standard piercing pin as well as with some other types of proprietary piercing pins and convertible piercing pins. The port assembly 12A will accommodate vented and non-vented piercing pin designs. The port assembly 12A is especially suitable for use with ISO standard length piercing pins having a length of about 1.102 inch and a diameter of about 0.220 inch. Even pins that have a shorter length and smaller diameter (e.g., 0.850 inch length and 0.208 inch diameter) can be accommodated with the port assembly 12A having the preferred dimensions described above.

The port assembly 12A accommodates the various piercing pins with an insertion force which is qualitatively acceptable to experienced users and with a withdrawal force that is not so excessive as to prevent normal removal and re-use of the administration of the piercing pin. Further, the withdrawal force required to remove the piercing pin is not so small that a user looses confidence that the pin was firmly held in its inserted position during use to deliver fluid from the container 10A. When the port assembly 12A is molded from the preferred linear low density polyethylene material, such as the material sold under the designation Dowlex 3010, the insertion and withdrawal of forces are within the desired range. The residual flexural modulus of the material and the resulting frictional load prevents inadvertent withdrawal of the piercing pin.

The port assembly 12A accommodates use of shorter and longer piercing pins. When a longer piercing pin is used, the penetrator element 60A is pushed further into the container 10A. When a longer pin is used, protection against inadvertent puncture of the container of film 82A is provided by the relatively thick saddle 56A around the inlet end 52A and by the “diamond shaped” configuration of the saddle 56A around the inlet end 52A. This three-dimensional geometry relative to the tip of the penetrator element 60A minimizes the likelihood of damaging the sidewall of the container 10A.

The port assembly 12A functions well with a variety of different piercing pins without requiring an excessively high insertion force. Thus, the beveled tip of a piercing pin is less likely to be damaged upon engagement with the lower, distal end of the penetrator element 60A. Such beveled piercing pins are drawn to the center of the end of the penetrator element 60A without requiring high insertion forces that might lead to damage of the beveled tip of the pin.

As can be seen in FIG. 21, the lower end of the penetrator element 60A has an outwardly flaring opening 73A. At the bottom end of the penetrator element 60A, the maximum inside diameter of the opening 73A is greater than the diameter of the cylindrical surface defined by the tubular port member formation 57A below the penetrator element 60A. Thus, a piercing pin (e.g., pin 90A shown in FIGS. 29 and 30) is drawn toward the center of the penetrator element bottom opening 73A and is seated properly therein. A conically shaped pin would also be properly aligned and centered by the internal geometry.

The use of a deep, V-shaped flange or saddle 56A around the inlet end 52A of the tubular port member 50A readily accommodates and receives the film 82A of the flexible container 10A at the bottom of the container 10A. This configuration maximizes drainage of the liquid out of the container 10A. Further, the shape of the exterior surface of the saddle 56A and of the tubular port member 50A has been designed, in the preferred embodiment illustrated in FIGS. 13–30, to provide a comfortable, ergonomic grip surface which is free of sharp corners that might cause finger discomfort and/or which might tear rubber gloves.

When the penetrator element 60A is advanced against the diaphragm 55A, the seal at the shoulder 53A between the film 82A and the shoulder surfaces 53A' and 53A" are stressed. The angle of stress is much greater than the natural peelable seal stress angle. Typically, peelable seals are stressed at 90 degrees or less. A seal stressed at greater than 90 degrees, and, especially, close to 180 degrees, is known to better resist delamination. The unique configuration of the sealing shoulder 53A provides an appropriate stress angle which resists such potential delamination and allows a significant force to be applied to the diaphragm 55A so as to penetrate the diaphragm 55A without causing delamination or other failure of the seal at the shoulder 53A.

Figure 31:
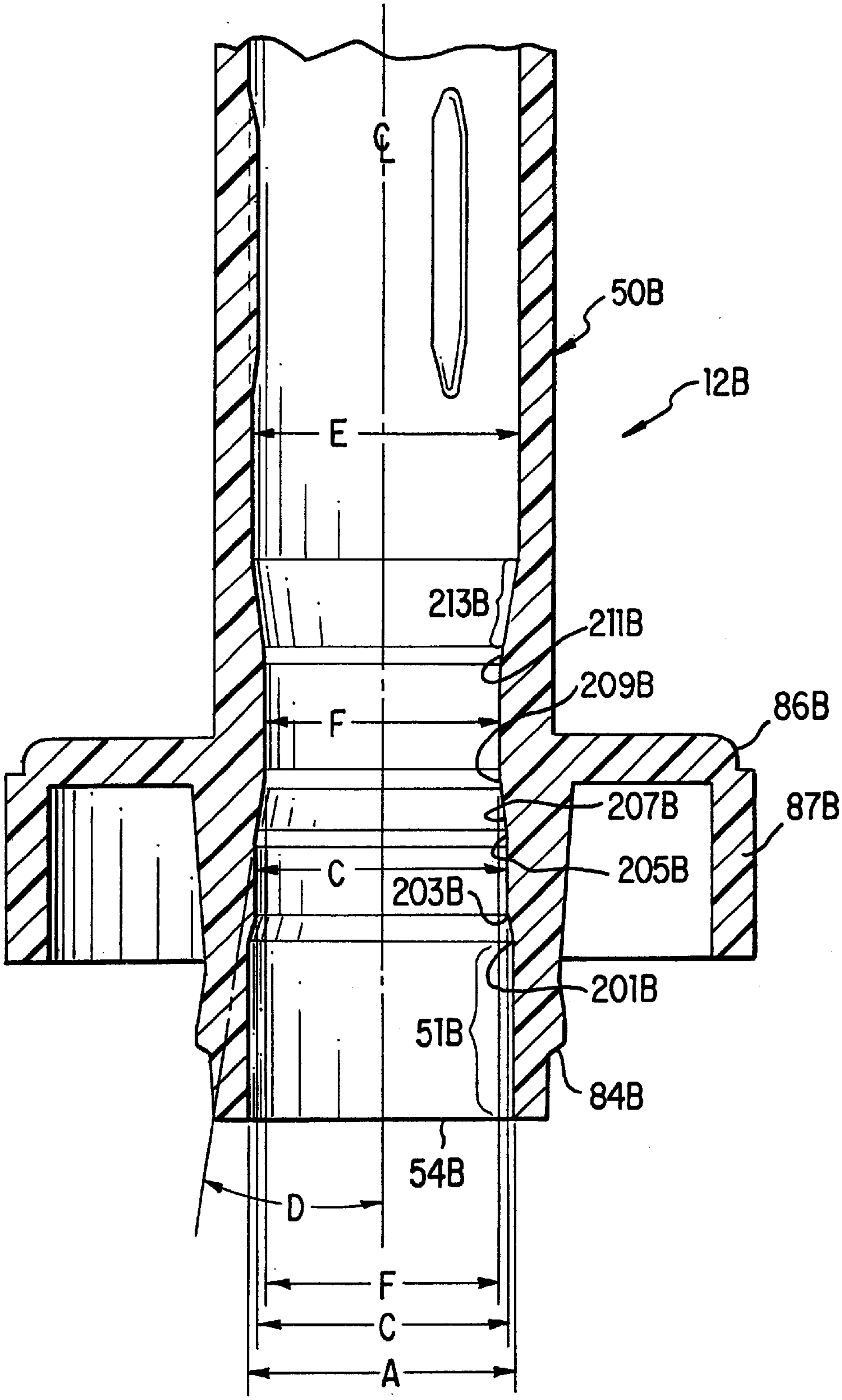
FIG. 31 is a view similar to FIG. 17, but FIG. 31 is a fragmentary view showing only the lower end of a third, and presently preferred, embodiment of the tubular port member of the present invention.

Although the above-described second embodiment of the port assembly 12A functions very well and provides desirable features, it has been found that the distal discharge end can be modified to provide a structure which is more easily manufactured and which accommodates high speed production manufacturing techniques utilizing mold process short cycle times (e.g., 20 seconds). Such a modification is illustrated in FIG. 31 which shows a third embodiment of the tubular port member designated generally by the reference numeral 12B. The third embodiment 12B is identical with the second embodiment 12A described above with reference to FIGS. 13–30 except that the port assembly 12B of the third embodiment has a port member 50B that has an internal configuration at the lower end or discharge end which differs somewhat from the internal configuration of the lower end or discharge end of the port member 50A of the second embodiment of the port assembly 12A. The different internal configuration of the discharge end of the third embodiment port member 50B accommodates molding of the port member 50B by means of conventional molding techniques with a relatively short mold cycle time (e.g., 20 seconds).

The port member 50B of the third embodiment of the port assembly 12B is adapted to receive and coact with a variety of conventional piercing pins, such as the piercing pin 90A described above with respect to the second embodiment illustrated in FIGS. 13–30. FIG. 31 is a fragmentary view which shows only the lower, discharge end of the third embodiment of the port member 50B, and the broken away upper portion of the port member 50B which is not shown is identical with the upper portion of the second embodiment of the port member 50A described above with reference to FIGS. 13–30, and the features, mode of operation, and advantages of the upper portion of the third embodiment of the port member 50B are the same as described above with respect to the upper portion of the second embodiment of the port member 50A.

As illustrated in FIG. 31, the port 50B defines a distal discharge end 54B which can accommodate the insertion of a piercing pin (such as piercing pin 90A described above with reference to the second embodiment illustrated in FIGS. 13–30). The distal-most opening at the discharge end 54B is defined within a discharge fitment 51B and, in the preferred embodiment, has a diameter A of 0.216 inch. The diameter decreases at a first concave radius 201B (as viewed from inside the port member 50B) and at a convex radius 203B (as viewed from inside the port member 50B). Each radius 201B and 203B is 0.015 inch.

The port member 50B has a next inwardly cylindrical portion having a diameter C which, in the preferred embodiment, is 0.203 inch. The inner end of the cylindrical portion of diameter C terminates at a radius 205B which is concave as viewed from inside the port member 50B. In the preferred embodiment, the radius 205B is 0.125 inch.

A tapered, frustoconical section 207B extends inwardly from the radius 205B. The angle of the taper of the section 207B is designated by the angle D in FIG. 31. In the preferred embodiment, the angle D is 7.65 degrees.

The inner end of the frustoconical surface 207B terminates in a radius 209B which is convex as viewed from inside the port member 50B. In the preferred embodiment, the radius 209B is 0.125 inch.

Inwardly of the radius 209B is a cylindrical section defined by the diameter F. In the preferred embodiment, the diameter F is 0.199 inch.

The inner end of the cylindrical section having the diameter F merges with a radius 211 B which is convex as viewed from inside the port member 50B. In the preferred embodiment, the radius 211B is 0.125 inch.

Inwardly of the radius 211B is a larger radius 213B. In the preferred embodiment, the radius 213B is concave as viewed from inside the port member 50B and is 0.78 inch. The inner end of the radius 213B merges with a cylindrical section having a diameter E. In the preferred embodiment, the diameter E is 0.210 inch, and this is the same as the diameter E of the corresponding cylindrical section of the second embodiment of the port member 50A described above with reference to FIG. 17.

As with the second embodiment of the port member 50A described above with reference to FIG. 17, the third embodiment of the port member 50B includes a flange 86B with an extending skirt 87B for engaging a cap, such as the cap 80A described above with reference to the second embodiment illustrated in FIGS. 13–30. The third embodiment skirt 87B is adapted to be deformed when subjected to heat or ultrasonic energy to effect a permanent set and to capture the cap in the same manner as described above with reference to the second embodiment illustrated in FIGS. 13–30. The outside of the fitment 51B of the third embodiment is preferably provided with a bead 84B for establishing frictional engagement between the cap (not illustrated) and the bead 84B.

The operation of the third embodiment of the port member 50B is substantially identical with the operation of the second embodiment of the port member 50A described above in detail with reference to FIGS. 13–30. Thus, one of a number of piercing pins having various lengths and varying slightly in diameter may be inserted into the third embodiment of the port member 50B. The third embodiment of the port member 50B is adapted to include an internally mounted penetrator element (not illustrated) which is identical with the penetrator element 60A of the second embodiment described above with reference to FIGS. 13–30. Such a penetrator element can be properly retained within the third embodiment of the port member 50B and is actuatable by insertion of a piercing pin to effect penetration of the film diaphragm (such as a diaphragm 55A of the second embodiment described above with reference to FIG. 30).

It will be appreciated that the radius 213B in the third embodiment of the port member 50B functions as an abutment shoulder to retain the penetrator element (not illustrated in FIG. 31 for the third embodiment). To this end, the radius 213B in FIG. 31 corresponds to the second embodiment abutment shoulder 57A' and functions analogously when the penetrator is in the fully retracted position. See, for example, how the second embodiment penetrator element 60A in the fully retracted position abuts the surface 57A' in FIG. 21. Movement of a penetrator upwardly in the third embodiment of the port member 50B, and its interaction with the other structures of the port member 50B, are identical with the movement and interaction in respect of the second embodiment of the assembly described above with reference to FIGS. 13–30.

While only some embodiments of the invention have been described, modifications within the scope of the present invention may be readily apparent to one of ordinary skill in the art. All such modifications are intended to be covered by the scope of the accompanying claims.

What is claimed is:

1. A port assembly for use with a flexible container formed from a film folded to define opposing sidewalls having portions sealed together to define a chamber, said port assembly comprising:

a hollow tubular port member having a distal discharge end and a proximal inlet end, said port member defining an annular sealing shoulder adjacent said inlet end against which the exterior surface of said film can be heat sealed to define radially inwardly thereof a generally circular, pierceable diaphragm, said annular sealing shoulder including (a) a radially inner, generally planar, annular first surface; and (b) a radially outer, generally arcuate, annular second surface extending from said first surface, said second surface having a transverse cross section which in part defines an arc of a circle and said second surface defining an annular groove for receiving a portion of said film to be heat-sealed thereto; and a hollow penetrator element slidably disposed in said tubular port member for movement between a fully retracted position away from said inlet end and a fully advanced position adjacent said inlet end to puncture said film diaphragm whereby fluid can flow out of said chamber through said hollow penetrator element and said port member.

2. The port assembly in accordance with claim 1 in which:

said port assembly is adapted for use with a container in which said film includes at least two layers and defines a generally V-shaped trough at the bottom of the container; and said port member includes a generally V-shaped saddle that can be heat-sealed to an exterior surface of said film at the bottom of said V-shaped trough.

3. The port assembly in accordance with claim 1 in which:

said penetrator element has a beveled distal end adapted to penetrate said film; and said penetrator element is adapted to puncture said film without said penetrator element being moved completely to said fully advanced position.

4. The port in accordance with claim 1 in which said tubular port member has a reduced diameter entry port at said distal discharge end adapted to sealingly engage the exterior surface of a piercing pin inserted therein.

5. The port assembly in accordance with claim 1 in which said tubular port member includes:

(1) an internal, proximal formation having an abutment shoulder defining a frustoconical surface against which a portion of said penetrator element abuts when said penetrator element is in said fully advanced position;

(2) an internal, distal formation having an abutment shoulder defining a frustoconical surface which is engaged by a portion of said penetrator element when said penetrator element is in said fully retracted position; and (3) an internal, intermediate formation between said proximal and distal formations, said intermediate formation including circumferentially spaced ribs which initially retain said penetrator element in said retracted position until said penetrator element is subjected to at least a predetermined minimum axial force acting toward the proximal direction.

6. A port assembly for use with a flexible container formed from a film folded to define a trough from which extend two opposing sidewalls having portions sealed together to define a chamber adjacent said trough, said port assembly comprising:

a hollow tubular port member having a distal discharge end and a proximal inlet end, said port member including a generally V-shaped saddle around said inlet end for being sealed to the exterior surface of said film at the bottom of said trough, said saddle including diverging planar regions for being sealed to the exterior surface of said film;

said port member defining an annular sealing shoulder at said inlet end against which the exterior surface of said film can be heat-sealed to define radially inwardly thereof a generally circular pierceable diaphragm, said annular sealing shoulder includes a radially inner, generally planar, annular first surface and a radially outer, generally arcuate, annular second surface extending from said first surface, said second surface having a transverse cross section which in part defines an arc of a circle and said second surface defining an annular groove for receiving a portion of said film to be heat-sealed thereto; and a hollow penetrator element slidably disposed in said tubular port member for movement between a fully retracted position away from said inlet end and a fully advanced position adjacent said inlet end to puncture said film at the bottom of said trough whereby fluid can flow out of said chamber though said hollow penetrator element and port member.

7. A port assembly for use with a flexible container formed from a film folded to define opposing sidewalls having portions sealed together to define a chamber, said port assembly comprising:

a hollow tubular port member having a distal discharge end and having a proximal inlet end which can be heat-sealed to the exterior surface of said film;

said port member defines an annular sealing shoulder at said inlet end against which the exterior surface of said film can be heat-sealed to define radially inwardly thereof a generally circular, pierceable diaphragm, said annular sealing shoulder includes a radially inner, generally planar, annular, first surface and a radially outer, generally arcuate, annular, second surface extending from said first surface, said second surface having a transverse cross section which in part defines an arc of a circle and said second surface defining an annular groove for receiving a portion of said film to be heat-sealed thereto;

a hollow penetrator element slidably disposed in said tubular port member for movement between a fully retracted position away from said inlet end and a fully advanced position adjacent said inlet end to puncture said film whereby fluid can flow out of said chamber though said hollow penetrator element and said port member; and said tubular port member having (1) an internal, proximal formation having an abutment shoulder defining a frustoconical surface against which a portion of said penetrator element abuts when said penetrator element is at said fully advanced position, (2) an internal, distal formation which is engaged by a portion of said penetrator element when said penetrator element is in said fully retracted position, and (3) an internal, intermediate formation between said internal proximal and distal formations for guiding said penetrator element through an initial part of the travel of said penetrator element as said penetrator element moves away from said fully retracted position.

8. A port assembly for use with a flexible container formed from a film folded to define opposing sidewalls having portions sealed together to define a chamber, said port assembly comprising:

a hollow tubular port member having a distal discharge end and a proximal inlet end, said port member defining an annular sealing shoulder adjacent said inlet end against which the exterior surface of said film is heat sealed to define radially inwardly thereof a generally circular, pierceable diaphragm, said sealing shoulder having a portion recessed within said port member inlet end;

said annular sealing shoulder having a radially inner, generally round, annular first surface having a transverse cross section which generally defines a portion of a circle and a radially outer, generally arcuate, annular, second surface extending from said first surface, said second surface having a transverse cross section which in part defines an arc of a circle and said second surface defining an annular groove in which a portion of said film is heat sealed thereto; and a hollow penetrator element slidably disposed in said tubular port member for movement between a fully retracted position away from said inlet end and a fully advanced position adjacent said inlet end to puncture said film diaphragm whereby fluid can flow out of said chamber through said hollow penetrator element and said port member.

9. A port assembly for use with a flexible container formed from a film folded to define opposing sidewalls having portions sealed together to define a chamber, said port assembly comprising:

a hollow tublar port member having a distal discharge end and a proximal inlet end, said port member defining an annular sealing shoulder adjacent said inlet end against which the exterior surface of said film is sealed by heat to define radially inwardly thereof a generally circular, pierceable diaphragm, said annular shoulder including a radially inner, annular first surface and a radially outer, generally arcuate, annular, second surface extending from said first surface, said second surface having a transverse cross section which in part defines an arc of a circle and said second surface defining an annular groove in which a portion of said film is heat sealed thereto, said annular shoulder being deformable under said heat, from a first state prior to heat deformation in which said radially inner, annular first surface is generally planar shaped to a second state subsequent to heat deformation in which said radially, annular first surface is generally rounded in shape and has a transverse cross section which defines an arc of a circle; and a hollow penetrator element slidably disposed in said tubular port member for movement between a fully retracted position away from said inlet end and a fully advanced position adjacent said inlet end to puncture said film diaphragm whereby fluid can flow out of said chamber through said hollow penetrator element and said port member.

* * * * *

UNITED STATES PATENT AND TRADEMARK OFFICE

CERTIFICATE OF CORRECTION

PATENT NO. : 6,280,431 B1 
DATED : August 28, 2001
INVENTOR(S) : John Domkowski et al.

It is certified that error appears in the above-identified patent and that said Letters Patent is hereby corrected as shown below:

Title page,
Item [75], Inventors, replace "Ron Coules, Punk Gorda," with -- Ron Coules, Punta Gorda --.

Signed and Sealed this

Fourth Day of June, 2002

*Attest:*

JAMES E. ROGAN

*Attesting Officer* *Director of the United States Patent and Trademark Office*